(12) United States Patent
Kurokawa et al.

(10) Patent No.: US 9,204,849 B2
(45) Date of Patent: Dec. 8, 2015

(54) RADIATION DETECTION PANEL, RADIATION IMAGING DEVICE, AND DIAGNOSTIC IMAGING DEVICE

(71) Applicant: Semiconductor Energy Laboratory Co., Ltd., Atsugi-shi, Kanagawa-ken (JP)

(72) Inventors: Yoshiyuki Kurokawa, Sagamihara (JP); Takayuki Ikeda, Atsugi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 547 days.

(21) Appl. No.: 13/959,778

(22) Filed: Aug. 6, 2013

(65) Prior Publication Data

US 2014/0056405 A1 Feb. 27, 2014

(30) Foreign Application Priority Data

Aug. 24, 2012 (JP) ................................ 2012-184985

(51) Int. Cl.
*G01T 1/20* (2006.01)
*A61B 6/00* (2006.01)

(52) U.S. Cl.
CPC ............. *A61B 6/4208* (2013.01); *G01T 1/2018* (2013.01)

(58) Field of Classification Search
CPC ..... H04N 5/3597; H04N 5/353; H04N 5/361; A61B 6/4233
See application file for complete search history.

(56) References Cited

U.S. PATENT DOCUMENTS

| 5,731,613 A | 3/1998 | Yamazaki et al. |
|---|---|---|
| 5,731,856 A | 3/1998 | Kim et al. |

(Continued)

FOREIGN PATENT DOCUMENTS

| EP | 0933673 B1 | 9/2004 |
|---|---|---|
| EP | 1737044 A | 12/2006 |

(Continued)

OTHER PUBLICATIONS

Fortunato.E et al., "Wide-Bandgap High-Mobility ZnO Thin-Film Transistors Produced at Room Temperature,", Appl. Phys. Lett. (Applied Physics Letters), Sep. 27, 2004, vol. 85, No. 13, pp. 2541-2543.

(Continued)

*Primary Examiner* — Hoon Song
(74) *Attorney, Agent, or Firm* — Eric J. Robinson; Robinson Intellectual Property Law Office, P.C.

(57) ABSTRACT

To achieve a radiation detection panel capable of outputting a signal for generating an accurate pixel signal regardless of the performance of a conversion unit, a detection circuit that outputs a signal used for generating a pixel signal includes a first output circuit that outputs a signal due to afterglow, and a second output circuit that outputs a signal including both a signal based on radiation emission and a signal due to afterglow. Transistors using an oxide semiconductor material for a channel formation region are used as some transistors included in the first and second output circuits. In the radiation detection panel having this structure, the signal (a first signal or a second signal) can be held in each output circuit; therefore, after all output circuits hold the signal (the first signal or the second signal), the first signal and the second signal can be sequentially output from detection circuits.

20 Claims, 15 Drawing Sheets

(56) References Cited

U.S. PATENT DOCUMENTS

| | | | |
|---|---|---|---|
| 5,744,864 A | 4/1998 | Cillessen et al. | |
| 5,923,722 A * | 7/1999 | Schulz | 378/98.8 |
| 6,025,607 A | 2/2000 | Ohori et al. | |
| 6,198,799 B1 | 3/2001 | Ono et al. | |
| 6,294,274 B1 | 9/2001 | Kawazoe et al. | |
| 6,563,174 B2 | 5/2003 | Kawasaki et al. | |
| 6,727,522 B1 | 4/2004 | Kawasaki et al. | |
| 6,747,638 B2 | 6/2004 | Yamazaki et al. | |
| 7,049,190 B2 | 5/2006 | Takeda et al. | |
| 7,061,014 B2 | 6/2006 | Hosono et al. | |
| 7,064,346 B2 | 6/2006 | Kawasaki et al. | |
| 7,105,868 B2 | 9/2006 | Nause et al. | |
| 7,211,825 B2 | 5/2007 | Shih et al | |
| 7,271,835 B2 | 9/2007 | Iizuka et al. | |
| 7,282,782 B2 | 10/2007 | Hoffman et al. | |
| 7,297,977 B2 | 11/2007 | Hoffman et al. | |
| 7,323,356 B2 | 1/2008 | Hosono et al. | |
| 7,385,224 B2 | 6/2008 | Ishii et al. | |
| 7,402,506 B2 | 7/2008 | Levy et al. | |
| 7,411,209 B2 | 8/2008 | Endo et al. | |
| 7,453,065 B2 | 11/2008 | Saito et al. | |
| 7,453,087 B2 | 11/2008 | Iwasaki | |
| 7,462,862 B2 | 12/2008 | Hoffman et al. | |
| 7,465,958 B2 | 12/2008 | Arao et al. | |
| 7,468,304 B2 | 12/2008 | Kaji et al. | |
| 7,501,293 B2 | 3/2009 | Ito et al. | |
| 7,525,523 B2 | 4/2009 | Yamazaki et al. | |
| 7,663,165 B2 | 2/2010 | Mouli | |
| 7,674,650 B2 | 3/2010 | Akimoto et al. | |
| 7,732,819 B2 | 6/2010 | Akimoto et al. | |
| 2001/0046027 A1 | 11/2001 | Tai et al. | |
| 2002/0056838 A1 | 5/2002 | Ogawa | |
| 2002/0132454 A1 | 9/2002 | Ohtsu et al. | |
| 2003/0189401 A1 | 10/2003 | Kido et al. | |
| 2003/0218222 A1 | 11/2003 | Wager et al. | |
| 2004/0038446 A1 | 2/2004 | Takeda et al. | |
| 2004/0127038 A1 | 7/2004 | Carcia et al. | |
| 2005/0017302 A1 | 1/2005 | Hoffman | |
| 2005/0199959 A1 | 9/2005 | Chiang et al. | |
| 2006/0035452 A1 | 2/2006 | Carcia et al. | |
| 2006/0043377 A1 | 3/2006 | Hoffman et al. | |
| 2006/0091793 A1 | 5/2006 | Baude et al. | |
| 2006/0108529 A1 | 5/2006 | Saito et al. | |
| 2006/0108636 A1 | 5/2006 | Sano et al. | |
| 2006/0110867 A1 | 5/2006 | Yabuta et al. | |
| 2006/0113536 A1 | 6/2006 | Kumomi et al. | |
| 2006/0113539 A1 | 6/2006 | Sano et al. | |
| 2006/0113549 A1 | 6/2006 | Den et al. | |
| 2006/0113565 A1 | 6/2006 | Abe et al. | |
| 2006/0157760 A1 | 7/2006 | Hayashi et al. | |
| 2006/0169973 A1 | 8/2006 | Isa et al. | |
| 2006/0170111 A1 | 8/2006 | Isa et al. | |
| 2006/0197092 A1 | 9/2006 | Hoffman et al. | |
| 2006/0208977 A1 | 9/2006 | Kimura | |
| 2006/0228974 A1 | 10/2006 | Thelss et al. | |
| 2006/0231882 A1 | 10/2006 | Kim et al. | |
| 2006/0238135 A1 | 10/2006 | Kimura | |
| 2006/0244107 A1 | 11/2006 | Sugihara et al. | |
| 2006/0284171 A1 | 12/2006 | Levy et al. | |
| 2006/0284172 A1 | 12/2006 | Ishii | |
| 2006/0292777 A1 | 12/2006 | Dunbar | |
| 2007/0018075 A1 | 1/2007 | Cazaux et al. | |
| 2007/0024187 A1 | 2/2007 | Shin et al. | |
| 2007/0046191 A1 | 3/2007 | Saito | |
| 2007/0052025 A1 | 3/2007 | Yabuta | |
| 2007/0054507 A1 | 3/2007 | Kaji et al. | |
| 2007/0090365 A1 | 4/2007 | Hayashi et al. | |
| 2007/0108446 A1 | 5/2007 | Akimoto | |
| 2007/0152217 A1 | 7/2007 | Lai et al. | |
| 2007/0172591 A1 | 7/2007 | Seo et al. | |
| 2007/0187678 A1 | 8/2007 | Hirao et al. | |
| 2007/0187760 A1 | 8/2007 | Furuta et al. | |
| 2007/0194379 A1 | 8/2007 | Hosono et al. | |
| 2007/0252928 A1 | 11/2007 | Ito et al. | |
| 2007/0272922 A1 | 11/2007 | Kim et al. | |
| 2007/0287296 A1 | 12/2007 | Chang | |
| 2008/0006877 A1 | 1/2008 | Mardilovich et al. | |
| 2008/0038882 A1 | 2/2008 | Takechi et al. | |
| 2008/0038929 A1 | 2/2008 | Chang | |
| 2008/0050595 A1 | 2/2008 | Nakagawara et al. | |
| 2008/0054319 A1 | 3/2008 | Mouli | |
| 2008/0073653 A1 | 3/2008 | Iwasaki | |
| 2008/0083950 A1 | 4/2008 | Pan et al. | |
| 2008/0106191 A1 | 5/2008 | Kawase | |
| 2008/0128689 A1 | 6/2008 | Lee et al. | |
| 2008/0129195 A1 | 6/2008 | Ishizaki et al. | |
| 2008/0166834 A1 | 7/2008 | Kim et al. | |
| 2008/0182358 A1 | 7/2008 | Cowdery-Corvan et al. | |
| 2008/0224133 A1 | 9/2008 | Park et al. | |
| 2008/0254569 A1 | 10/2008 | Hoffman et al. | |
| 2008/0258139 A1 | 10/2008 | Ito et al. | |
| 2008/0258140 A1 | 10/2008 | Lee et al. | |
| 2008/0258141 A1 | 10/2008 | Park et al. | |
| 2008/0258143 A1 | 10/2008 | Kim et al. | |
| 2008/0296568 A1 | 12/2008 | Ryu et al. | |
| 2009/0068773 A1 | 3/2009 | Lai et al. | |
| 2009/0072321 A1 | 3/2009 | Arao et al. | |
| 2009/0073325 A1 | 3/2009 | Kuwabara et al. | |
| 2009/0101948 A1 | 4/2009 | Park et al. | |
| 2009/0114910 A1 | 5/2009 | Chang | |
| 2009/0134399 A1 | 5/2009 | Sakakura et al. | |
| 2009/0152506 A1 | 6/2009 | Umeda et al. | |
| 2009/0152541 A1 | 6/2009 | Maekawa et al. | |
| 2009/0278122 A1 | 11/2009 | Hosono et al. | |
| 2009/0280600 A1 | 11/2009 | Hosono et al. | |
| 2009/0295769 A1 | 12/2009 | Yamazaki et al. | |
| 2010/0065844 A1 | 3/2010 | Tokunaga | |
| 2010/0092800 A1 | 4/2010 | Itagaki et al. | |
| 2010/0109002 A1 | 5/2010 | Itagaki et al. | |
| 2010/0117991 A1 | 5/2010 | Koyama et al. | |
| 2010/0182282 A1 | 7/2010 | Kurokawa et al. | |
| 2011/0176038 A1 | 7/2011 | Kurokawa et al. | |
| 2011/0215323 A1 | 9/2011 | Kurokawa et al. | |
| 2011/0220889 A1 | 9/2011 | Kurokawa et al. | |
| 2011/0221723 A1 | 9/2011 | Kurokawa et al. | |
| 2012/0001076 A1 * | 1/2012 | Chappo et al. | 250/362 |
| 2012/0002090 A1 | 1/2012 | Aoki et al. | |
| 2012/0056861 A1 | 3/2012 | Kurokawa et al. | |
| 2012/0146027 A1 | 6/2012 | Tamura et al. | |
| 2013/0083227 A1 * | 4/2013 | Murata et al. | 348/308 |

FOREIGN PATENT DOCUMENTS

| | | |
|---|---|---|
| EP | 2226847 A | 9/2010 |
| JP | 60-198861 A | 10/1985 |
| JP | 63-210022 A | 8/1988 |
| JP | 63-210023 A | 8/1988 |
| JP | 63-210024 A | 8/1988 |
| JP | 63-215519 A | 9/1988 |
| JP | 63-239117 A | 10/1988 |
| JP | 63-265818 A | 11/1988 |
| JP | 05-251705 A | 9/1993 |
| JP | 08-264794 A | 10/1996 |
| JP | 11-505377 | 5/1999 |
| JP | 11-316428 A | 11/1999 |
| JP | 2000-044236 A | 2/2000 |
| JP | 2000-150900 A | 5/2000 |
| JP | 2002-076356 A | 3/2002 |
| JP | 2002-289859 A | 10/2002 |
| JP | 2003-086000 A | 3/2003 |
| JP | 2003-086808 A | 3/2003 |
| JP | 2004-103957 A | 4/2004 |
| JP | 2004-273614 A | 9/2004 |
| JP | 2004-273732 A | 9/2004 |
| WO | WO-2004/114391 | 12/2004 |

OTHER PUBLICATIONS

Dembo.H et al., "RFCPUS on Glass and Plastic Substrates Fabricated by TFT Transfer Technology,", IEDM 05: Technical Digest of International Electron Devices Meeting, Dec. 5, 2005, pp. 1067-1069.

(56) References Cited

OTHER PUBLICATIONS

Ikeda.T et al., "Full-Functional System Liquid Crystal Display Using Cg-Silicon Technology,", SID Digest '04 : SID International Symposium Digest of Technical Papers, 2004, vol. 35, pp. 860-863.

Nomura.K et al., "Room-Temperature Fabrication of Transparent Flexible Thin-Film Transistors Using Amorphous Oxide Semiconductors,", Nature, Nov. 25, 2004, vol. 432, pp. 488-492.

Park.J et al., "Improvements in the Device Characteristics of Amorphous Indium Gallium Zinc Oxide Thin-Film Transistors by Ar Plasma Treatment,", Appl. Phys. Lett. (Applied Physics Letters), Jun. 26, 2007, vol. 90, No. 26, pp. 262106-1-262106-3.

Takahashi.M et al., "Theoretical Analysis of IgZO Transparent Amorphous Oxide Semiconductor,", IDW '08 : Proceedings of the 15th International Display Workshops, Dec. 3, 2008, pp. 1637-1640.

Hayashi.R et al., "42.1: Invited Paper: Improved Amorphous In—Ga—Zn—O TFTs,", SID Digest '08 : SID International Symposium Digest of Technical Papers, May 20, 2008, vol. 39, pp. 621-624.

Prins.M et al., "A Ferroelectric Transparent Thin-Film Transistor,", Appl. Phys. Lett. (Applied Physics Letters), Jun. 17, 1996, vol. 68, No. 25, pp. 3650-3652.

Nakamura.M et al., "The phase relations in the In2O3—Ga2ZnO4—ZnO system at 1350° C.,", Journal of Solid State Chemistry, Aug. 1, 1991, vol. 93, No. 2, pp. 298-315.

Kimizuka.N et al., "Syntheses and Single-Crystal Data of Homologous Compounds, In2O3(ZnO)m (m=3, 4, and 5), InGaO3(ZnO)3, and Ga2O3(ZnO)m (m=7, 8, 9, 16) in the In2O3—ZnGa2O4—ZnO System,", Journal of Solid State Chemistry, Apr. 1, 1995, vol. 116, No. 1, pp. 170-178.

Nomura.K et al., "Thin-Film Transistor Fabricated in Single-Crystalline Transparent Oxide Semiconductor,", Science, May 23, 2003, vol. 300, No. 5623, pp. 1269-1272.

Masuda.S et al., "Transparent thin film transistors using ZnO as an active channel layer and their electrical properties,", J. Appl. Phys. (Journal of Applied Physics), Feb. 1, 2003, vol. 93, No. 3, pp. 1624-1630.

Asakuma.N et al., "Crystallization and Reduction of Sol-Gel-Derived Zinc Oxide Films by Irradiation With Ultraviolet Lamp,", Journal of Sol-Gel Science and Technology, 2003, vol. 26, pp. 181-184.

Osada.T et al., "15.2: Development of Driver-Integrated Panel using Amorphous In—Ga—Zn—Oxide TFT,", SID International Symposium Digest of Technical Papers, May 31, 2009, pp. 184-187.

Nomura.K et al., "Carrier transport in transparent oxide semiconductor with intrinsic structural randomness probed using single-crystalline InGaO3(ZnO)5 films,", Appl. Phys. Lett. (Applied Physics Letters), Sep. 13, 2004, vol. 85, No. 11, pp. 1993-1995.

Li.C et al., "Modulated Structures of Homologous Compounds InMO3(ZnO)m (M=In,Ga; m=Integer) Described by Four-Dimensional Superspace Group,", Journal of Solid State Chemistry, 1998, vol. 139, pp. 347-355.

Son.K et al., "42.4L: Late-News Paper: 4 Inch QVGA AMOLED Driven by the Threshold Voltage Controlled Amorphous GIZO (Ga2O3—In2O3—ZnO) TFT,", SID Digest '08 : SID International Symposium Digest of Technical Papers, May 20, 2008, vol. 39, pp. 633-636.

Lee.J et al., "World's Largest (15-Inch) XGA AMLCD Panel Using IGZO Oxide TFT,", SID Digest '08 : SID International Symposium Digest of Technical Papers, May 20, 2008, vol. 39, pp. 625-628.

Nowatari.H et al., "60.2: Intermediate Connector With Suppressed Voltage Loss for White Tandem OLEDs,", SID Digest '09 : SID International Symposium Digest of Technical Papers, May 31, 2009, vol. 40, pp. 899-902.

Kanno.H et al., "White Stacked Electrophosphorecent Organic Light-Emitting Devices Employing MOO3 as a Charge-Generation Layer,", Adv. Mater. (Advanced Materials), 2006, vol. 18, No. 3, pp. 339-342.

Tsuda.K et al., "Ultra Low Power Consumption Technologies for Mobile TFT-LCDs,", IDW '02 : Proceedings of the 9th International Display Workshops, Dec. 4, 2002, pp. 295-298.

Van de Walle.C, "Hydrogen as a Cause of Doping in Zinc Oxide,", Phys. Rev. Lett. (Physical Review Letters), Jul. 31, 2000, vol. 85, No. 5, pp. 1012-1015.

Fung.T et al., "2-D Numerical Simulation of High Performance Amorphous In—Ga—Zn—O TFTs for Flat Panel Displays,", AM-FPD '08 Digest of Technical Papers, Jul. 2, 2008, pp. 251-252, The Japan Society of Applied Physics.

Jeong.J et al., "3.1: Distinguished Paper: 12.1-Inch WXGA AMOLED Display Driven by Indium—Gallium—Zinc Oxide TFTs Array,", SID Digest '08 : SID International Symposium Digest of Technical Papers, May 20, 2008, vol. 39, No. 1, pp. 1-4.

Park.J et al., "High performance amorphous oxide thin film transistors with self-aligned top-gate structure,", IEDM 09: Technical Digest of International Electron Devices Meeting, Dec. 7, 2009, pp. 191-194.

Kurokawa.Y et al., "UHF RFCPUS on Flexible and Glass Substrates for Secure RFID Systems,", Journal of Solide-State Circuits, 2008, vol. 43, No. 1, pp. 292-299.

Ohara.H et al., "Amorphous In—Ga—Zn—Oxide TFTs with Suppressed Variation for 4.0 inch QVGA AMOLED Display,", AP-FPD '09 Digest of Technical Papers, Jul. 1, 2009, pp. 227-230, The Japan Society of Applied Physics.

Coates.D et al., "Optical Studies of the Amorphous Liquid-Cholesteric Liquid Crystal Transition:The "Blue Phase",", Physics Letters, Sep. 10, 1973, vol. 45A, No. 2, pp. 115-116.

Cho.D et al., "21.2:Al and Sn-Doped Zinc Indium Oxide Thin Film Transistors for AMOLED Back-Plane,", SID Digest '09 : SID International Symposium Digest of Technical Papers, May 31, 2009, pp. 280-283.

Lee.M et al., "15.4:Excellent Performance of Indium—Oxide-Based Thin-Film Transistors by DC Sputtering,", SID Digest '09 : SID International Symposium Digest of Technical Papers, May 31, 2009, pp. 191-193.

Jin.D et al., "65.2:Distinguished Paper:World-Largest (6.5") Flexible Full Color Top Emission AMOLED Display on Plastic Film and Its Bending Properties,", SID Digest '09 : SID International Symposium Digest of Technical Papers, May 31, 2009, pp. 983-985.

Sakata.J et al., "Development of 4.0-In. AMOLED Display With Driver Circuit Using Amorphous In—Ga—Zn—Oxide TFTs,", IDW '09 : Proceedings of the 16th International Display Workshops, 2009, pp. 689-692.

Park.J et al., "Amorphous Indium—Gallium—Zinc Oxide Tfts and Their Application for Large Size AMOLED,", AM-FPD '08 Digest of Technical Papers, Jul. 2, 2008, pp. 275-278.

Park.S et al., "Challenge to Future Displays: Transparent AM-OLED Driven by PEALD Grown ZnO TFT,", IMID '07 Digest, 2007, pp. 1249-1252.

Godo.H et al., "Temperature Dependence of Characteristics and Electronic Structure for Amorphous In—Ga—Zn—Oxide TFT,", AM-FPD '09 Digest of Technical Papers, Jul. 1, 2009, pp. 41-44.

Osada.T et al., "Development of Driver-Integrated Panel Using Amorphous In—Ga—Zn—Oxide TFT,", AM-FPD '09 Digest of Technical Papers, Jul. 1, 2009, pp. 33-36.

Hirao.T et al., "Novel Top-Gate Zinc Oxide Thin-Film Transistors (ZnO TFTs) for AMLCDs,", Journal of the SID, 2007, vol. 15, No. 1, pp. 17-22.

Hosono.H, "68.3:Invited Paper:Transparent Amorphous Oxide Semiconductors for High Performance TFT,", SID Digest '07 : SID International Symposium Digest of Technical Papers, 2007, vol. 38, pp. 1830-1833.

Godo.H et al., "P-9:Numerical Analysis on Temperature Dependence of Characteristics of Amorphous In—Ga—Zn—Oxide TFT,", SID Digest '09 : SID International Symposium Digest of Technical Papers, May 31, 2009, pp. 1110-1112.

Ohara.H et al., "21.3:4.0 In. QVGA AMOLED Display Using In—Ga—Zn—Oxide TFTs With a Novel Passivation Layer,", SID Digest '09 : SID International Symposium Digest of Technical Papers, May 31, 2009, pp. 284-287.

Miyasaka.M, "SUFTLA Flexible Microelectronics on Their Way to Business,", SID Digest '07 : SID International Symposium Digest of Technical Papers, 2007, vol. 38, pp. 1673-1676.

(56) References Cited

OTHER PUBLICATIONS

Chern.H et al., "An Analytical Model for the Above-Threshold Characteristics of Polysilicon Thin-Film Transistors,", IEEE Transactions on Electron Devices, Jul. 1, 1995, vol. 42, No. 7, pp. 1240-1246.

Kikuchi.H et al., "39.1:Invited Paper:Optically Isotropic Nano-Structured Liquid Crystal Composites for Display Applications,", SID Digest '09 : SID International Symposium Digest of Technical Papers, May 31, 2009, pp. 578-581.

Asaoka.Y et al., "29.1:Polarizer-Free Reflective LCD Combined With Ultra Low-Power Driving Technology,", SID Digest '09 : SID International Symposium Digest of Technical Papers, May 31, 2009, pp. 395-398.

Lee.H et al., "Current Status of, Challenges to, and Perspective View of AM-OLED ,", IDW '06 : Proceedings of the 13th International Display Workshops, Dec. 7, 2006, pp. 663-666.

Kikuchi.H et al., "62.2:Invited Paper:Fast Electro-Optical Switching in Polymer-Stabilized Liquid Crystalline Blue Phases for Display Application,", SID Digest '07 : SID International Symposium Digest of Technical Papers, 2007, vol. 38, pp. 1737-1740.

Nakamura.M, "Synthesis of Homologous Compound with New Long-Period Structure,", NIRIM Newsletter, Mar. 1, 1995, vol. 150, pp. 1-4.

Kikuchi.H et al., "Polymer-Stabilized Liquid Crystal Blue Phases,", Nature Materials, Sep. 2, 2002, vol. 1, pp. 64-68.

Kimizuka.N. et al., "Spinel,YbFe2O4, and Yb2Fe3O7 Types of Structures for Compounds in the In2O3 and Sc2O3—A2O3—BO systems [A; Fe, Ga, or Al; B: Mg, Mn, Fe, Ni, Cu,or Zn] at Temperatures over 1000° C.,", Journal of Solid State Chemistry, 1985, vol. 60, pp. 382-384.

Kitzerow.H et al., "Observation of Blue Phases in Chiral Networks,", Liquid Crystals, 1993, vol. 14, No. 3, pp. 911-916.

Costello.M et al., "Electron Microscopy of a Cholesteric Liquid Crystal and Its Blue Phase,", Phys. Rev. A (Physical Review. A), May 1, 1984, vol. 29, No. 5, pp. 2957-2959.

Meiboom.S et al., "Theory of the Blue Phase of Cholesteric Liquid Crystals,", Phys. Rev. Lett. (Physical Review Letters), May 4, 1981, vol. 46, No. 18, pp. 1216-1219.

Park.Sang-Hee et al., "42.3: Transparent ZnO Thin Film Transistor for the Application of High Aperture Ratio Bottom Emission AM-OLED Display,", SID Digest '08 : SID International Symposium Digest of Technical Papers, May 20, 2008, vol. 39, pp. 629-632.

Orita.M et al., "Mechanism of Electrical Conductivity of Transparent InGaZnO4,", Phys. Rev. B (Physical Review. B), Jan. 15, 2000, vol. 61, No. 3, pp. 1811-1816.

Nomura.K et al., "Amorphous Oxide Semiconductors for High-Performance Flexible Thin-Film Transistors,", Jpn. J. Appl. Phys. (Japanese Journal of Applied Physics) , 2006, vol. 45, No. 5B, pp. 4303-4308.

Janotti.A et al., "Native Point Defects in ZnO,", Phys. Rev. B (Physical Review. B), Oct. 4, 2007, vol. 76, No. 16, pp. 165202-1-165202-22.

Park.J et al., "Electronic Transport Properties of Amorphous Indium—Gallium—Zinc Oxide Semiconductor Upon Exposure to Water,", Appl. Phys. Lett. (Applied Physics Letters) , 2008, vol. 92, pp. 072104-1-072104-3.

Hsieh.H et al., "P-29:Modeling of Amorphous Oxide Semiconductor Thin Film Transistors and Subgap Density of States,", SID Digest '08 : SID International Symposium Digest of Technical Papers, 2008, vol. 39, pp. 1277-1280.

Janotti.A et al., "Oxygen Vacancies in ZnO,", Appl. Phys. Lett. (Applied Physics Letters) , 2005, vol. 87, pp. 122102-1-122102-3.

Oba.F et al., "Defect energetics in ZnO: A hybrid Hartree-Fock density functional study,", Phys. Rev. B (Physical Review. B), 2008, vol. 77, pp. 245202-1-245202-6.

Orita.M et al., "Amorphous transparent conductive oxide InGaO3(ZnO)m (m<4):a Zn4s conductor,", Philosophical Magazine, 2001, vol. 81, No. 5, pp. 501-515.

Hosono.H et al., "Working hypothesis to explore novel wide band gap electrically conducting amorphous oxides and examples,", J. Non-Cryst. Solids (Journal of Non-Crystalline Solids), 1996, vol. 198-200, pp. 165-169.

Mo.Y et al., "Amorphous Oxide TFT Backplanes for Large Size AMOLED Displays,", IDW '08 : Proceedings of the 6th International Display Workshops, Dec. 3, 2008, pp. 581-584.

Kim.S et al., "High-Performance oxide thin film transistors passivated by various gas plasmas,", 214th ECS Meeting, 2008, No. 2317, ECS.

Clark.S et al., "First Principles Methods Using CASTEP,", Zeitschrift fur Kristallographie, 2005, vol. 220, pp. 567-570.

Lany.S et al., "Dopability, Intrinsic Conductivity, and Nonstoichiometry of Transparent Conducting Oxides,", Phys. Rev. Lett. (Physical Review Letters), Jan. 26, 2007, vol. 98, pp. 045501-1-045501-4.

Park.J et al., "Dry etching of ZnO films and plasma-induced damage to optical properties,", J. Vac. Sci. Technol. B (Journal of Vacuum Science & Technology B), Mar. 1, 2003, vol. 21, No. 2, pp. 800-803.

Oh.M et al., "Improving the Gate Stability of ZnO Thin-Film Transistors With Aluminum Oxide Dielectric Layers,", J. Electrochem. Soc. (Journal of the Electrochemical Society), 2008, vol. 155, No. 12, pp. H1009-H1014.

Ueno.K et al., "Field-Effect Transistor on SrTiO3 With Sputtered Al2O3 Gate Insulator,", Appl. Phys. Lett. (Applied Physics Letters) , Sep. 1, 2003, vol. 83, No. 9, pp. 1755-1757.

Tanaka.K et al., "45.5: A System LCD with Optical Input Function using Infra-Red Backlight Subtraction Scheme,", SID Digest '10 : SID International Symposium Digest of Technical Papers, 2010, pp. 680-683.

Jeon.S et al., "180nm Gate Length Amorphous InGaZnO Thin Film Transistor for High Density Image Sensor Applications,", IEDM 10: Technical Digest of International Electron Devices Meeting, Dec. 6, 2010, pp. 504-507.

* cited by examiner

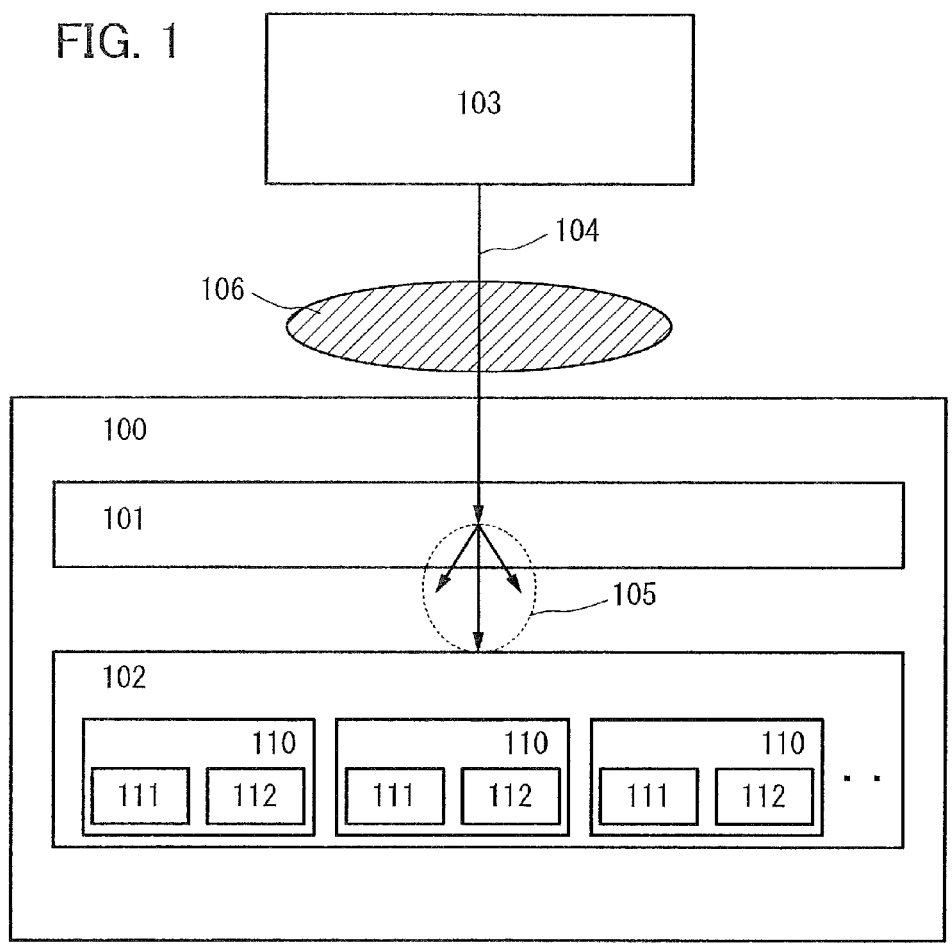

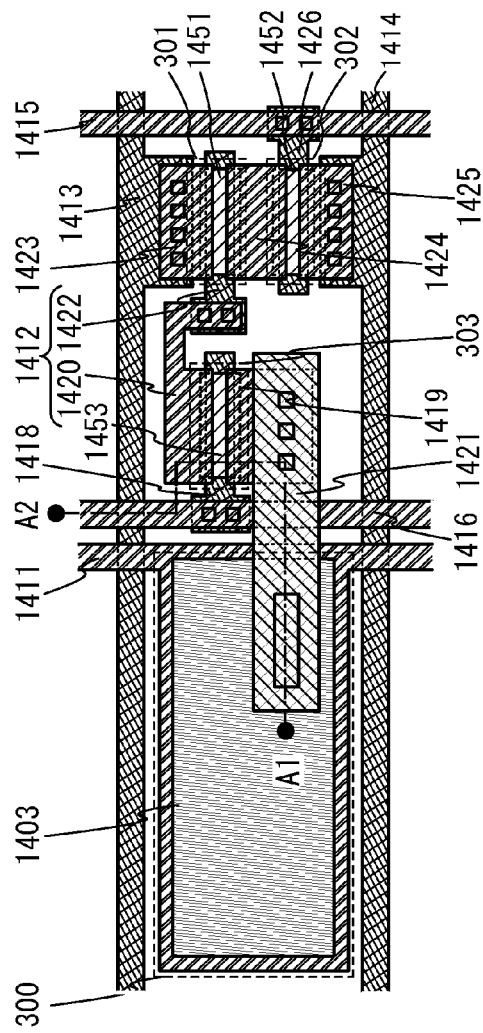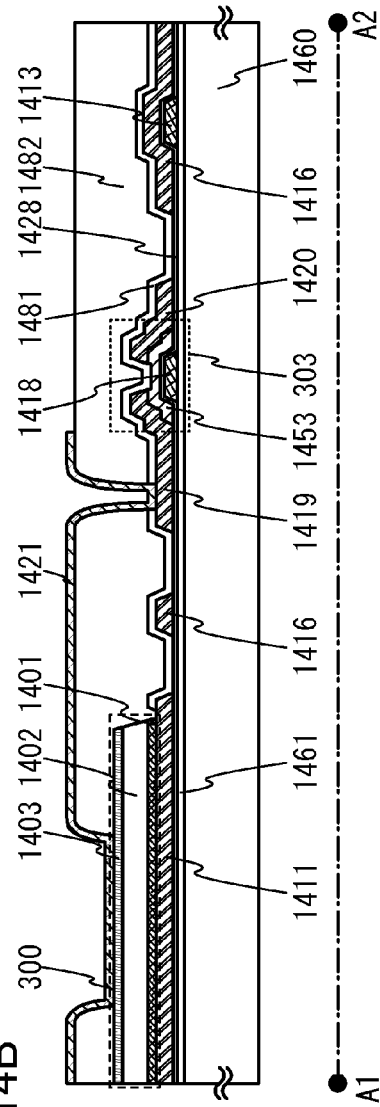
FIG. 14A
FIG. 14B

RADIATION DETECTION PANEL, RADIATION IMAGING DEVICE, AND DIAGNOSTIC IMAGING DEVICE

BACKGROUND OF THE INVENTION

1. Field of the Invention

The present invention relates to a radiation detection panel and a radiation imaging device including the radiation detection panel. The radiation imaging device particularly relates to a diagnostic imaging device in which a radiation source can emit X-rays.

2. Description of the Related Art

A device that images an object with radiation (hereinafter referred to as a radiation imaging device) is used in various applications in medical and industrial fields; for example, in the medical field, a diagnostic imaging device that images the inside of a human body with X-rays is widely used in medical practice.

With a conventional diagnostic imaging device using X-rays, an X-ray source emits X-rays to a specific part (e.g., a bone or a lung) of a patient, and X-rays passing through the part are projected on a photographic film or the like. Then, the photographic film is developed, so that the inside of the specific part can be visualized.

In the case of employing a photographic film, a method of digitizing imaging data is commonly used because storage of photographic films, that is, storage of data after imaging is troublesome.

An example of a method of digitizing imaging data is a method of using an imaging plate and a bio-imaging analyzer. In this method, a plate (am imaging plate) in which a material layer that emits light when being irradiated with X-rays (such properties are referred to as stimulability or photostimulable properties) is formed on a support is used, and X-rays passing through a specific part of a patient are projected on the imaging plate. After X-ray projection, light emitted from the plate is detected with a bio-imaging analyzer, whereby imaging data is constituted to obtain digitized data.

Although imaging data can be digitized by the method, the process is complicated because an image is first obtained as analog data by the imaging plate and then is digitized by the bio-imaging analyzer.

For this reason, instead of the above method, a radiation imaging device that obtains digital imaging data with the use of a radiation detection panel (also referred to as a flat panel detector) has recently received attention (e.g., see Patent Document 1).

The radiation detection panel is composed of a conversion unit that converts radiation (e.g., X-rays) emitted from a radiation source into charge or light (e.g., visible light), and a detection unit that includes a plurality of detection circuits for detecting the charge or the light. Imaging data of an object can be digitized by being composed of signals output from the detection unit.

In a direct conversion flat panel detector, charge is generated directly from radiation, and a detection circuit generates an output signal with the use of the charge.

On the other hand, in an indirect conversion flat panel detector, radiation is first converted into light (e.g., a conversion unit generates visible light by being irradiated with X-rays), the light is further converted into charge, and a detection circuit generates an output signal with the use of the charge.

REFERENCE

Patent Document 1: Japanese Published Patent Application No. H11-316428

SUMMARY OF THE INVENTION

In order to make an appropriate diagnosis of fine contrast of the affected area by a radiation imaging device including the radiation detection panel, it is necessary that a signal constituting imaging data of the object (the signal is hereinafter referred to as a pixel signal) correctly represent the amount of radiation entering the conversion unit of the radiation detection panel (i.e., the amount of radiation passing through the object).

In a conversion unit (e.g., a scintillator) of a radiation detection panel with indirect conversion, there occurs a phenomenon in which light emission continues even after radiation emission stops (which is called afterglow). However, when an interval long enough to sufficiently reduce afterglow is provided between stop of radiation emission (A1 in FIG. 11A) and the next radiation emission (A2 in FIG. 11A) as shown in FIG. 11A, for example, adverse effect of afterglow on a signal output from a detection circuit can be reduced.

However, application for taking moving images (or temporally continuous still images), for example, for monitoring blood flow in vessels needs to increase the time resolution of a radiation imaging device to obtain high-definition images; thus, it is desired that a period after stop of X-ray irradiation before start of the next X-ray irradiation be as short as possible.

When a period after stop of X-ray irradiation before start of the next X-ray irradiation is short as described above, the next X-ray irradiation starts while a signal due to afterglow in the conversion unit is output from the detection circuit. Accordingly, as shown in FIG. 11B, a signal resulting from addition of signals due to the previous and earlier afterglows (corresponding to a region 1101 in FIG. 11B) to a signal based on radiation emission (corresponding to a region 1100 in FIG. 11B) is output from the detection circuit and serves as a pixel signal.

For this reason, if a period after stop of X-ray irradiation before start of the next X-ray irradiation is short and a signal output from the detection circuit of the radiation detection panel is used as a pixel signal without change, a difference arises between the amount of radiation entering the conversion unit of the radiation detection panel and imaging data of the object.

There has been recently developed a conversion unit in which afterglow is very small (i.e., decay of light emission after stop of radiation emission is fast and afterglow disappears (or becomes negligible) in an extremely short time); however, the conversion unit with such characteristics is generally expensive and thus its use is limited. In particular, a radiation imaging device that includes a plurality of conversion units or a large-area conversion unit, for example, becomes extremely expensive by using the conversion unit with very small afterglow.

In view of the foregoing problems, an object of one embodiment of the invention disclosed herein is to provide a radiation detection panel that outputs signals for generating an accurate pixel signal regardless of the performance of a conversion unit.

Another object of one embodiment of the invention disclosed herein is to provide a radiation imaging device that includes the radiation detection panel with the above characteristics and has high resolution to obtain a high-definition image.

In order to achieve these objects, a pixel signal should not include a signal due to afterglow.

In view of this, in one embodiment of the invention disclosed herein, a detection circuit that outputs signals used for generating one pixel signal is composed of a first output circuit that outputs a first signal including information on light emission due to afterglow, and a second output circuit that outputs a second signal including both information on light emission based on radiation emission and information on light emission due to afterglow.

The reasons the two output circuits are provided in the detection circuit are described below with reference to FIG. 12.

First, before radiation emission, the first output circuit detects the amount of light incident from a conversion unit in a period M (the amount corresponds to a region 1200 in FIG. 12). This amount of the incident light is due to afterglow in the conversion unit.

Then, the second output circuit detects the amount of light incident from the conversion unit in a period N (the amount corresponds to a region 1201 in FIG. 12). This incident light includes light from the conversion unit based on radiation emission and light from the conversion unit due to afterglow. For easy understanding of the concept, the period M and the period N are the same in length in FIG. 12.

In general, the light from the conversion unit due to afterglow is drastically decreased in a time as short as several milliseconds after the end of radiation emission, and then gradually decreased. Thus, the amount of incident light due to afterglow in the period M and that in the period N become closer as the period M and the period N become shorter.

In such a manner, the first output circuit outputs a signal based on the amount of light incident from the conversion unit in the period M (hereinafter, the signal output from the first output circuit is called "first signal"), and the second output circuit outputs a signal based on the amount of light incident from the conversion unit in the period N (hereinafter, the signal output from the second output circuit is called "second signal"). Accordingly, a pixel signal can be produced using a difference between both these signals and as a result, accurate imaging data of an object can be obtained.

In the detection unit, detection of the amount of light incident from the conversion unit in the period M by the first output circuit and detection of the amount of light incident from the conversion unit in the period N by the second output circuit are sequentially performed in all detection circuits, and then the first signal and the second signal are output from each of the detection circuits. Accordingly, the first output circuit and the second output circuit included in each detection circuit need to hold data (which can also be represented as charge or potential) generated based on the amount of light incident from the conversion unit, at least until all the detection circuits complete the detection process.

In view of this, in one embodiment of the invention disclosed herein, in order not to leak data generated by the first output circuit based on the amount of light incident from the conversion unit and data generated by the second output circuit based on the amount of light incident from the conversion unit, each of the first and second output circuits is configured to hold the data between a drain (or a source) of a transistor using an oxide semiconductor material for a channel formation region and a gate of another transistor.

The bandgap of a film using an oxide semiconductor material is greater than or equal to 3.0 eV (electron volts), which is much wider than the bandgap of silicon (1.1 eV).

The off-resistance of a transistor (resistance between a source and a drain of the transistor in an off state) is inversely proportional to the concentration of carriers thermally excited in a channel formation region. Since the bandgap of silicon is 1.1 eV even in a state where there is no carrier caused by a donor or an acceptor (i.e., even in the case of an intrinsic semiconductor), the concentration of thermally excited carriers at room temperature (200 K) is approximately $1 \times 10^{11}$ $cm^{-3}$.

The bandgap of a film using an oxide semiconductor material is generally as wide as 3.0 eV or more as described above, and the concentration of thermally excited carriers in a film with a bandgap of 3.2 eV, for example, is approximately $1 \times 10^{-7}$ $cm^{-3}$. When the electron mobility is the same, the resistivity is inversely proportional to the carrier concentration, and thus the resistivity of the semiconductor with a bandgap of 3.2 eV is 18 orders of magnitude higher than that of silicon.

Since a transistor that uses such a wide bandgap oxide semiconductor material for a channel formation region can achieve extremely low off-state current, using the transistor in the above manner enables data generated based on the amount of light incident from the conversion unit to be held in the first output circuit and the second output circuit for a long time.

Thus, the first output circuit and the second output circuit can hold data based on the amount of light incident from the conversion unit (hereinafter the data in the first output circuit is referred to as first data and the data in the second output circuit is referred to as second data) until all the detection circuits complete the detection process.

After all the detection circuits complete the detection process, each of the detection circuits outputs a signal generated using the first data (hereinafter the signal is referred to as the first signal) and a signal generated using the second data (hereinafter the signal is referred to as the second signal).

One embodiment of the present invention is a radiation detection panel including a conversion unit configured to convert radiation into light, and a detection unit including a plurality of detection circuits each having a first output circuit and a second output circuit. The first output circuit and the second output circuit each include a photoelectric conversion element generating charge in response to light incident from the conversion unit, a first transistor in which a gate potential varies in accordance with the amount of the charge, a second transistor controlling a signal output from the first transistor, and a third transistor that holds the gate potential of the first transistor and uses an oxide semiconductor material for a channel formation region. The first output circuit generates first data corresponding to the amount of charge generated by the photoelectric conversion element when radiation is not emitted, and holds the first data. The second output circuit generates second data corresponding to the amount of charge generated by the photoelectric conversion element when radiation is emitted, and holds the second data. The detection unit outputs a first signal generated using the first data and a second signal generated using the second data from each of the detection circuits after the first data is held in all the first output circuits and the second data is held in all the second output circuits in the detection unit.

In the radiation detection panel having the above structure, a signal component due to afterglow in the conversion unit can be eliminated, resulting in achievement of a radiation detection panel in which signals for generating an accurate pixel signal is obtained regardless of the performance of the conversion unit.

Detailed connections between the photoelectric conversion element and the first to third transistors in the aforementioned radiation detection panel are as follows. One of electrodes of the photoelectric conversion element is electrically connected to a first wiring, and the other is electrically connected to one of a source and a drain of the third transistor. One of a source and a drain of the first transistor is electrically connected to a second wiring, and the other is electrically connected to one of a source and a drain of the second transistor. The other of the source and the drain of the second transistor is electrically connected to a third wiring. A gate of the second transistor is electrically connected to a fourth wiring. The other of the source and the drain of the third transistor is electrically connected to a gate of the first transistor. A gate of the third transistor is electrically connected to a fifth wiring.

In the radiation detection panel, it is preferable that the first output circuit and the second output circuit used for generating one pixel signal be provided adjacent to each other, because an accurate pixel signal is difficult to obtain when they are placed apart from each other.

The length of a time for the first output circuit to detect light (hereinafter also referred to as a first detection time) is preferably smaller than or equal to the length of a time for the second output circuit to detect light (hereinafter also referred to as a second detection time). As described above, the amount of light due to afterglow is approximately the same in the first detection time and the second detection time; however, the amount of light due to afterglow in the second detection time is sometimes smaller than that in the first detection time depending on the material used for the conversion unit. Consequently, making the first detection period shorter than the second detection period can adjust a reduction in the amount of light due to afterglow in the second detection period.

In the radiation detection panel, at least one of the first transistor and the second transistor provided in each of the first and second output circuits may include a channel formation region formed using an oxide semiconductor material.

A radiation imaging device capable of obtaining accurate imaging data can be achieved by a combination of the radiation detection panel, a radiation source, and a pixel signal generation unit that generates a pixel signal by using a difference between the first signal and the second signal output from the radiation detection panel.

One embodiment of the radiation imaging device is a diagnostic imaging device in which the radiation source is an X-ray radiation source and the conversion unit includes a scintillator converting X-rays into visible light. The diagnostic imaging device can diagnose an internal condition more correctly with a more accurate pixel signal and higher contrast. Moreover, the internal condition can be diagnosed correctly by obtainment of more segmented scan images by shortening each emission time for the radiation source and shortening an interval between detection operations, for example.

The detection circuit used for generating a pixel signal is composed of the first output circuit that outputs the first signal including information on light emission due to afterglow, and the second output circuit that outputs the second signal including both information on light emission based on radiation emission and information on light emission due to afterglow.

A transistor using an oxide semiconductor material for a channel formation region is used as some of the transistors included in the first and second output circuits.

In the radiation detection panel having the above structure, the signal (the first signal or the second signal) can be held in each of the output circuits; therefore, after all the output circuits hold the signal (the first signal or the second signal), the first signal and the second signal can be sequentially output from the detection circuits.

Then, pixel signals composing imaging data are produced using the first signals and the second signals that are output from the detection circuits included in the radiation detection panel.

With the use of the radiation detection panel in a radiation imaging device, the radiation imaging device can obtain accurate imaging data.

BRIEF DESCRIPTION OF THE DRAWINGS

In the accompanying drawings:

FIG. 1 illustrates the structure of a radiation detection panel;

FIGS. 14A and 14B illustrate the layout of a detection circuit; and

DETAILED DESCRIPTION OF THE INVENTION

Figure 2A:
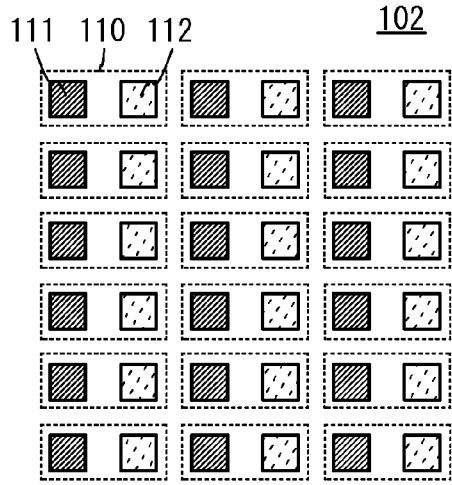
FIGS. 2A to 2E each illustrate the structure of a detection unit included in a radiation detection panel.

Embodiments will be hereinafter described in detail with reference to the accompanying drawings. Note that embodiments described below can be embodied in many different modes, and it is easily understood by those skilled in the art that modes and details can be variously changed without departing from the spirit and scope of the present invention. Therefore, the present invention should not be construed as being limited to the following description of the embodiments. In the drawings for explaining the embodiments, the same parts or parts having a similar function are denoted by the same reference numerals, and description of such parts is not repeated.

Note that in the embodiments described below, "one terminal" of a transistor refers to one of a source electrode and a drain electrode, and "the other terminal" of the transistor refers to the other of the source electrode and the drain electrode. That is, when one terminal of the transistor is the source electrode, the other terminal of the transistor refers to the drain electrode.

Embodiment 1

In Embodiment 1, the structure of a radiation detection panel will be described with reference to FIG. 1 and FIGS. 2A to 2E.

<Structure of Radiation Detection Panel>

An overview of the structure of a radiation detection panel will be described with reference to FIG. 1. In FIG. 1, a radiation detection panel 100 includes a conversion unit 101 that receives radiation 104 emitted from the outside and converts the radiation 104 into light, and a plurality of detection circuits 110 each including a first output circuit 111 and a second output circuit 112 each of which outputs a signal based on light 105 emitted from the conversion unit 101. Note that the radiation 104 is emitted from a radiation source 103 and enters the radiation detection panel 100. An object 106 is disposed between the radiation detection panel 100 and the radiation source 103.

The conversion unit 101 includes a substance that absorbs energy of incident radiation (e.g., X-rays, γ-rays, β-rays, or neutron rays) and emits light (e.g., infrared rays, visible light, or ultraviolet rays) or a material containing the substance; known examples of such a substance and such a material are a material such as $Gd_2O_2S$:Tb, $Gd_2O_2S$:Pr, $Gd_2O_2S$:Eu, BaF-Cl:Eu, CsI:Ti, ZnS:Ag, LiF:W, or LiI:Eu, and a resin or ceramics in which any of the above materials is dispersed. Note that the substance after the colon represents an impurity mixed to facilitate the capture of excited electrons.

A detection unit 102 includes the plurality of detection circuits 110 each including the first output circuit 111 and the second output circuit 112.

As described above, a pixel signal is generated using a first signal output from the first output circuit 111 and a second signal output from the second output circuit 112 in the detection circuit 110. Thus, for example, if the first output circuit and the second output circuit used for generating one pixel signal are placed apart from each other, an accurate pixel signal cannot be obtained in some cases.

That is, a pixel signal is preferably generated using a pair of the first output circuit 111 and the second output circuit 112 that can receive light emitted from the conversion unit 101 under substantially the same conditions (i.e., that are provided at positions at which lights emitted from one point of the conversion unit 101 have approximately the same intensity). Consequently, the first output circuit 111 and the second output circuit 112 used in a pair to produce a pixel signal are preferably provided adjacent to each other.

Figure 2B:
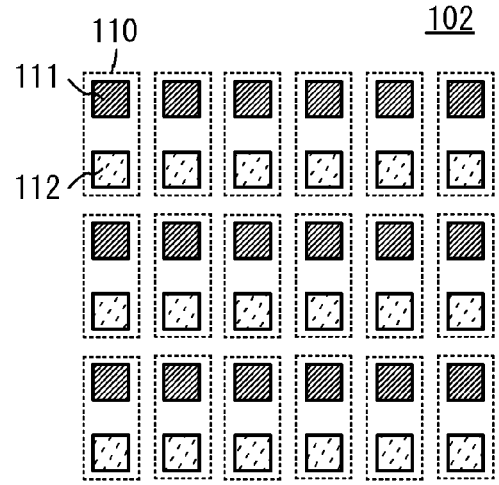
Figure 2C:
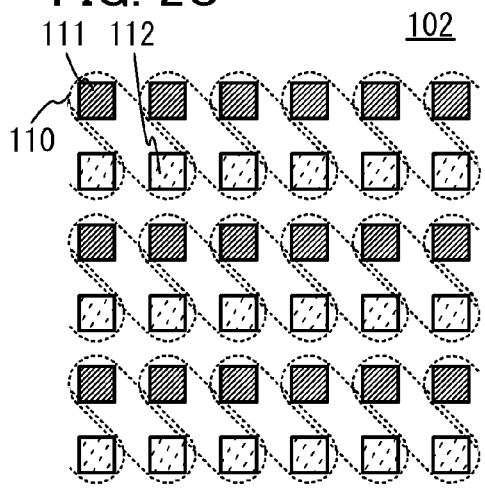

For example, the detection unit 102 seen from the above can have a structure in which a plurality of detection circuits 110 each have a pair of the first output circuit 111 and the second output circuit 112 adjacent in the horizontal direction as illustrated in FIG. 2A, a structure in which a plurality of detection circuits 110 each have a pair of the first output circuit 111 and the second output circuit 112 adjacent in the vertical direction as illustrated in FIG. 2B, or a structure in which a plurality of detection circuits 110 each have a pair of the first output circuit 111 and the second output circuit 112 adjacent in an oblique direction as illustrated in FIG. 2C.

Figure 2D:
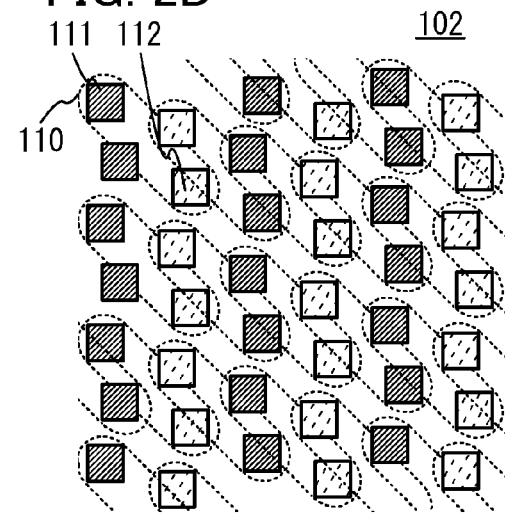

Note that the first output circuits 111 and the second output circuits 112 are not necessarily arranged neatly in a matrix, and for example, as illustrated in FIG. 2D, a plurality of detection circuits 110 each having a pair of the first output circuit 111 and the second output circuit 112 may be misaligned (i.e., one pair of the first output circuit 111 and the second output circuit 112 may not be aligned with another pair).

Figure 2E:
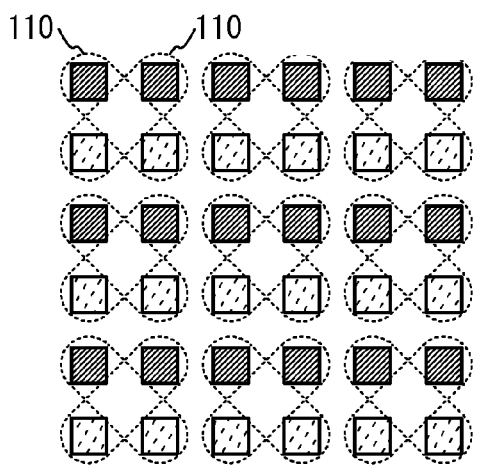

Alternatively, as illustrated in FIG. 2E, a plurality of detection circuits 110 each having a pair of the first output circuit 111 and the second output circuit 112 may cross each other (i.e., in such a manner that one pair of the first output circuit 111 and the second output circuit 112 crosses another pair).

Note that in the detection circuits 110 illustrated in FIGS. 2A to 2E, the first output circuit 111 and the second output circuit 112 may be placed in an inverted position. For example, in FIG. 2A, the first output circuit 111 is placed on the left side of the detection circuit 110 and the second output circuit 112 is placed on the right side of the detection circuit 110; however, the first output circuit 111 may be placed on the right side of the detection circuit 110 and the second output circuit 112 may be placed on the left side of the detection circuit 110.

<Configuration of Output Circuit>

An example of the configuration of the first output circuit 111 and the second output circuit 112 will be described below with reference to FIG. 3A. Note that the first output circuit 111 and the second output circuit 112 can have the same configuration.

Figure 3A:
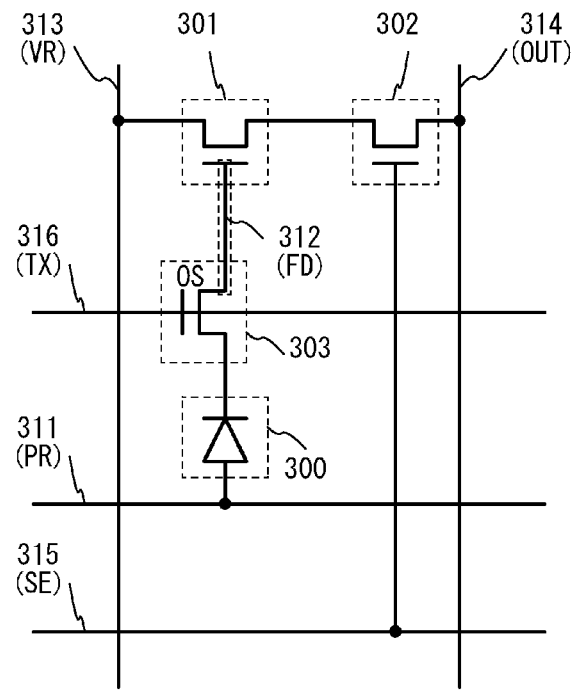
FIG. 3A illustrates the structure of a detection circuit.

As illustrated in FIG. 3A, the first output circuit 111 and the second output circuit 112 are configured to include a photoelectric conversion element 300 that generates charge in response to light emitted from the conversion unit 101, a first transistor 301 in which a potential applied to a gate varies in accordance with the amount of charge generated by the photoelectric conversion element 300, a second transistor 302 that controls a signal output from the first transistor 301, and a third transistor 303 that holds the potential applied to the gate of the first transistor 301 (also referred to as the potential of a second wiring 312).

One electrode of the photoelectric conversion element 300 is connected to a first wiring 311 (also referred to as a wiring PR).

The gate of the first transistor 301 is electrically connected to the second wiring 312 (also referred to as a wiring FD). One of a source and a drain of the first transistor 301 is electrically connected to a third wiring 313 (also referred to as a wiring VR). The other of the source and the drain of the first transistor 301 is electrically connected to one of a source and a drain of the second transistor 302.

The other of the source and the drain of the second transistor 302 is electrically connected to a fourth wiring 314 (also referred to as a wiring OUT). A gate of the second transistor 302 is electrically connected to a fifth wiring 315 (also referred to as a wiring SE).

Note that an integrator circuit may be connected to the fourth wiring 314 (OUT). Connecting the integrator circuit to the fourth wiring 314 (OUT) increases S/N, enabling detection of weaker light. A specific configuration example of the integrator circuit will be described in Embodiment 2.

One of a source and a drain of the third transistor 303 provided between the photoelectric conversion element 300 and the first transistor 301 is electrically connected to the other electrode of the photoelectric conversion element 300. The other of the source and the drain of the third transistor 303 is electrically connected to the second wiring 312 (FD). A gate of the third transistor 303 is electrically connected to a sixth wiring 316 (also referred to as a wiring TX).

Examples of the photoelectric conversion element 300 are an element that generates charge by receiving infrared rays, an element that generates charge by receiving visible light, and an element that generates charge by receiving ultraviolet rays.

The third transistor 303 in an off state needs to have a function of holding charge generated when the photoelectric conversion element 300 receives light, as a potential at the second wiring 312; consequently, the third transistor 303 needs to be a transistor with high mobility and extremely low off-state current. For this reason, an oxide semiconductor material is used for a channel formation region of the third transistor 303. In FIG. 3A, for easy understanding, "OS" is written beside the transistor using an oxide semiconductor material for a channel formation region.

The structure of the transistor using an oxide semiconductor material for a channel formation region will be described in detail in Embodiment 5.

The first transistor 301 can be a thin film transistor in which amorphous silicon, microcrystalline silicon, polycrystalline silicon, single crystal silicon, or the like is used for a channel formation region. Since the first transistor 301 is provided to amplify an electric signal generated by the photoelectric conversion element 300, the first transistor 301 needs high mobility. Moreover, the first transistor 301 needs low off-state current in order to prevent output of an unnecessary potential to the third wiring 313 (VR). For these reasons, it is also effective to use a transistor that uses an oxide semiconductor material achieving both high mobility and low off-state current in a channel formation region.

The second transistor 302 can be a thin film transistor in which amorphous silicon, microcrystalline silicon, polycrystalline silicon, single crystal silicon, or the like is used for a channel formation region. Since the second transistor 302 is provided to control an output from the detection circuit 110, the second transistor 302 needs high mobility. Further, the second transistor 302 needs low off-state current in order to prevent output of an unnecessary potential to the fourth wiring 314 (OUT). For these reasons, it is also effective to use a transistor that uses an oxide semiconductor material achieving both high mobility and low off-state current in a channel formation region.

The use of transistors using an oxide semiconductor material for a channel formation region as all the transistors included in the detection circuit 110 can simplify the process of fabricating the detection circuit.

When a semiconductor material capable of providing higher mobility than an oxide semiconductor material, such as polycrystalline or single crystal silicon, is used for the channel formation regions of the first transistor 301 and the second transistor 302, data can be read from the detection circuit 110 at high speed.

Connecting a capacitor to the fourth wiring 314 (OUT) is effective in stabilizing the potential of the fourth wiring 314 (OUT).

In FIG. 3A, the first transistor 301 and the second transistor 302 are electrically connected in series in this order between the third wiring 313 (VR) and the fourth wiring 314 (OUT); alternatively, the first transistor 301 and the second transistor 302 may be connected in reverse. That is, the second transistor 302 and the first transistor 301 may be electrically connected in series in this order between the third wiring 313 (VR) and the fourth wiring 314 (OUT).

In FIG. 3A, the third transistor 303 has a gate only on one side of a semiconductor layer; however, the third transistor 303 may have a pair of gates placed so that the semiconductor layer is sandwiched therebetween. When the third transistor 303 has a pair of gates placed so that the semiconductor layer is sandwiched therebetween, one of the gates can function as a front gate to which the potential of the second wiring 312 is applied, and the other gate can function as a backgate that controls the threshold voltage or the like of the third transistor 303. In this case, the potential applied to the other gate preferably ranges from −20 V to +2 V with reference to the source potential. If a change in the threshold voltage of the third transistor 303 does not adversely affect the operation of the detection circuit 110 when the potential applied to the other gate varies in the above range, the other gate may be electrically isolated (floating).

The above is the description of one example of the configuration of the first output circuit 111 and the second output circuit 112 included in the detection circuit 110. A layout example of the output circuit illustrated in FIG. 3A will be described in Embodiment 4.

<Operation Flow of Output Circuit>

The operation of the output circuit illustrated in FIG. 3A will be described with reference to a timing chart in FIG. 3B. Note that the first output circuit 111 and the second output circuit 112 can perform a read operation in the same manner.

Figure 3B:
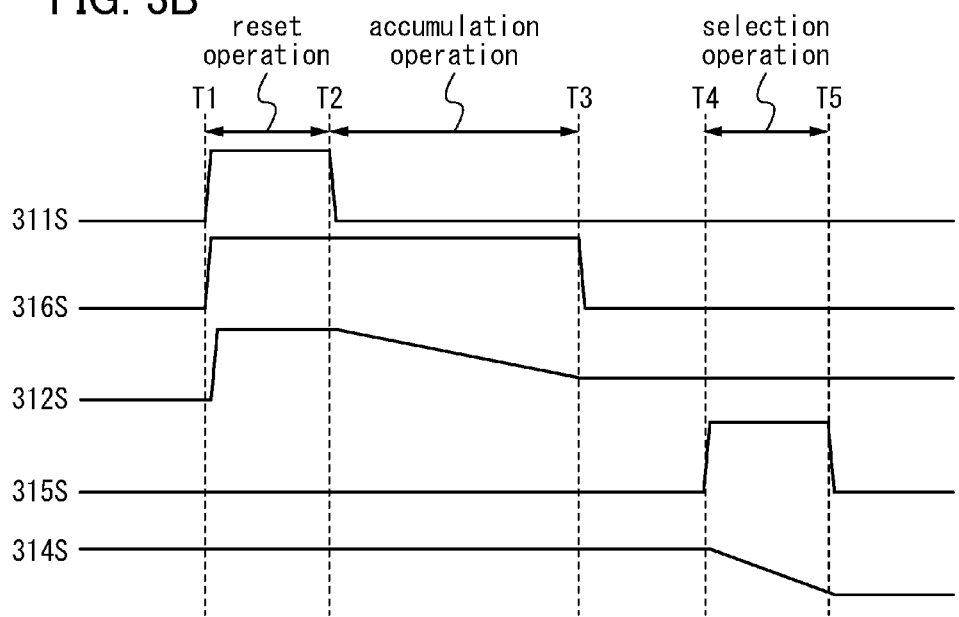
FIG. 3B is a chart showing the operation of the detection circuit.

In FIG. 3B, signals 311S, 312S, 314S, 315S, and 316S correspond to potentials of the first wiring 311 (PR), the second wiring 312 (FD), the fourth wiring 314 (OUT), the fifth wiring 315 (SE), and the sixth wiring 316 (TX) in FIG. 3A. The potential of the third wiring 313 (VR) is fixed at low level.

First, at a time T1, the potential of the first wiring 311 (PR) (the signal 311S) is set high and the potential of the sixth wiring 316 (TX) (the signal 316S) is set high (i.e., a reset operation starts), so that a forward bias is applied to the photoelectric conversion element 300 and the potential of the second wiring 312 (FD) (the signal 312S) becomes high. Note that the potential of the fourth wiring 314 (OUT) (the signal 314S) is precharged to high level.

Next, at a time T2, the potential of the first wiring 311 (PR) (the signal 311S) is set low and the potential of the sixth wiring 316 (TX) (the signal 316S) is kept high (i.e., the reset operation finishes and an accumulation operation starts), so that a photocurrent flows through the photoelectric conversion element 300 in response to light emitted from the conversion unit 101, and the potential of the second wiring 312 (FD) (the signal 312S) starts to be lowered.

Since the amount of photocurrent increases when the photoelectric conversion element 300 is irradiated with light, the speed of decrease in the potential of the second wiring 312 (FD) (the signal 312S) changes in accordance with the amount of emitted light. In other words, the channel resistance between the source and the drain of the first transistor 301 changes in accordance with the amount of light emitted to the photoelectric conversion element 300 from the conversion unit 101.

Then, at a time T3, the potential of the sixth wiring 316 (TX) (the signal 316S) is set low (i.e., the accumulation operation finishes).

Since the third transistor 303 is a transistor whose channel formation region is formed using an oxide semiconductor material as described above and thus has extremely low off-state current, the charge can be held at the second wiring 312 (FD), which is also referred to as the wiring between the other of the source and the drain of the third transistor and the gate of the first transistor, until a subsequent selection operation is performed. The amount of the charge corresponds to data held in the output circuit (first data in the first output circuit 111 and second data in the second output circuit 112).

Here, the potential of the second wiring 312 (FD) depends on the amount of charge generated by the photoelectric conversion element 300 during the accumulation operation. That is, the potential of the second wiring 312 (FD) changes in accordance with the amount of light emitted to the photoelectric conversion element 300 from the conversion unit 101.

Note that when the potential of the sixth wiring 316 (TX) (the signal 316S) is set low, the potential of the second wiring 312 (FD) sometimes changes because of parasitic capacitance between the sixth wiring 316 (TX) and the second wiring 312 (FD). A large amount of potential change makes it impossible to obtain an accurate amount of charge generated by the photoelectric conversion element 300 during the accumulation operation. Examples of effective measures to reduce the amount of potential change include reducing the capacitance between the gate and the source (or between the gate and the drain) of the third transistor 303, increasing the gate capacitance of the first transistor 301, and providing a storage capacitor to connect the second wiring 312 (FD). Note that in FIG. 3B, the potential change can be ignored by the adoption of these measures.

Then, at a time T4, the potential of the fifth wiring 315 (SE) (the signal 315S) is set high (i.e., the selection operation starts), so that the potential of the fourth wiring 314 (OUT) (the signal 314S) decreases. Note that precharge of the fourth wiring 314 (OUT) is terminated before the time T4.

Here, the speed of decrease in the potential of the fourth wiring 314 (OUT) (the signal 314S) depends on the channel resistance between the source and the drain of the first transistor 301. That is, this speed changes in accordance with the amount of light emitted to the photoelectric conversion element 300 from the conversion unit 101 during the accumulation operation.

Next, at a time T5, the potential of the fifth wiring 315 (SE) (the signal 315S) is set low (i.e., the selection operation finishes), so that a current flowing between the source and the drain of the second transistor 302 is interrupted and the potential of the fourth wiring 314 (OUT) (the signal 314S) becomes constant. This potential corresponds to a signal output from the output circuit (the first signal in the first output circuit 111 and the second signal in the second output circuit 112).

Here, the constant potential of the fourth wiring 314 (OUT) varies depending on the amount of light entering the photoelectric conversion element 300 from the conversion unit 101. Thus, by obtaining the potential of the fourth wiring 314 (OUT) (the signal 314S), the amount of light entering the photoelectric conversion element 300 from the conversion unit 101 during the accumulation operation can be found.

Specifically, as the amount of light entering the photoelectric conversion element 300 from the conversion unit 101 is larger, the potential of the second wiring 312 (FD) (the signal 312S) becomes lower and the gate potential of the first transistor 301 becomes lower; thus, the speed of decrease in the potential of the fourth wiring 314 (OUT) (the signal 314S) becomes lower. As a result, the potential of the fourth wiring 314 (OUT) (the signal 314S) is higher.

Further, as the amount of light entering the photoelectric conversion element 300 from the conversion unit 101 is smaller, the potential of the second wiring 312 (FD) (the signal 312S) becomes higher and the gate potential of the first transistor 301 becomes higher; thus, the speed of decrease in the potential of the fourth wiring 314 (OUT) (the signal 314S) becomes higher. As a result, the potential of the fourth wiring 314 (OUT) (the signal 314S) is lower.

As described above, the operation of the first output circuit 111 and the second output circuit 112 is performed by repetition of a sequence of the reset operation, the accumulation operation, and the selection operation.

Note that the configuration and operation flow of the first output circuit 111 and the second output circuit 112 are not limited to those illustrated in FIGS. 3A and 3B. A different configuration of the first output circuit 111 and the second output circuit 112 and the operation flow for the configuration will be described in Embodiment 3.

The operation of reading a signal from one output circuit included in the detection circuit 110 has been described so far. In order to achieve short-time imaging in the radiation detection panel, all the detection circuits need to perform the reset operation, the accumulation operation, and the selection operation at high speed. The operation flow of the entire detection unit 102 including a plurality of detection circuits 110 will be described below with reference to FIG. 4 and FIG. 5.

<Operation Flow of Entire Detection Unit>

Figure 4:
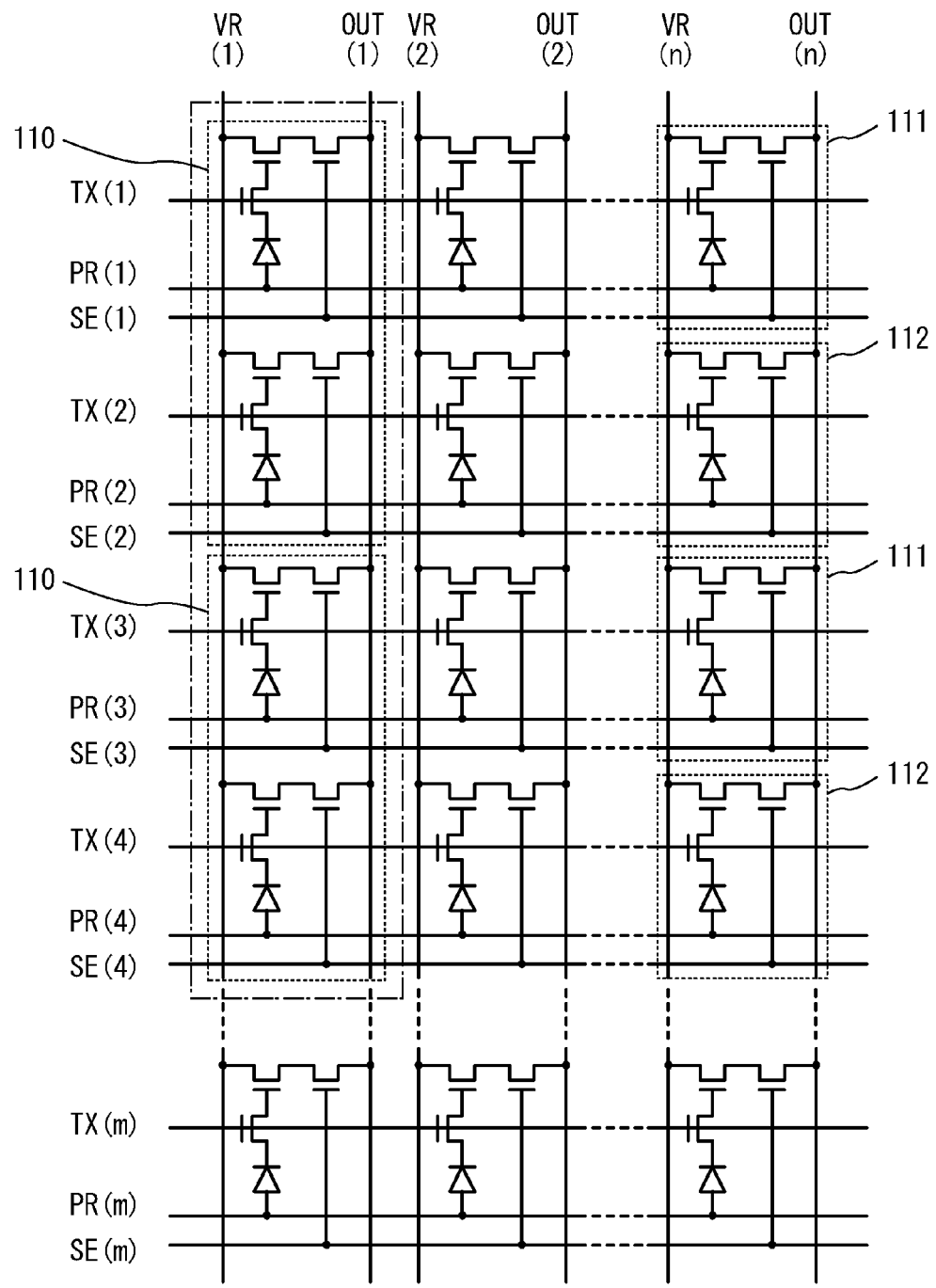
FIG. 4 illustrates the structure of a detection unit.

As illustrated in FIG. 4, the detection unit 102 includes the first output circuits 111 and the second output circuits 112 arranged in a matrix of m rows and n columns In the configuration, when counting from the top in the row direction, the first output circuits 111 are provided in odd-numbered rows and the second output circuits 112 are provided in even-numbered rows. That is, the plurality of detection circuits 110 have the structure illustrated in FIG. 2B, in which the first output circuit and the second output circuit used for producing a pixel signal are arranged in the vertical direction.

Figure 5:
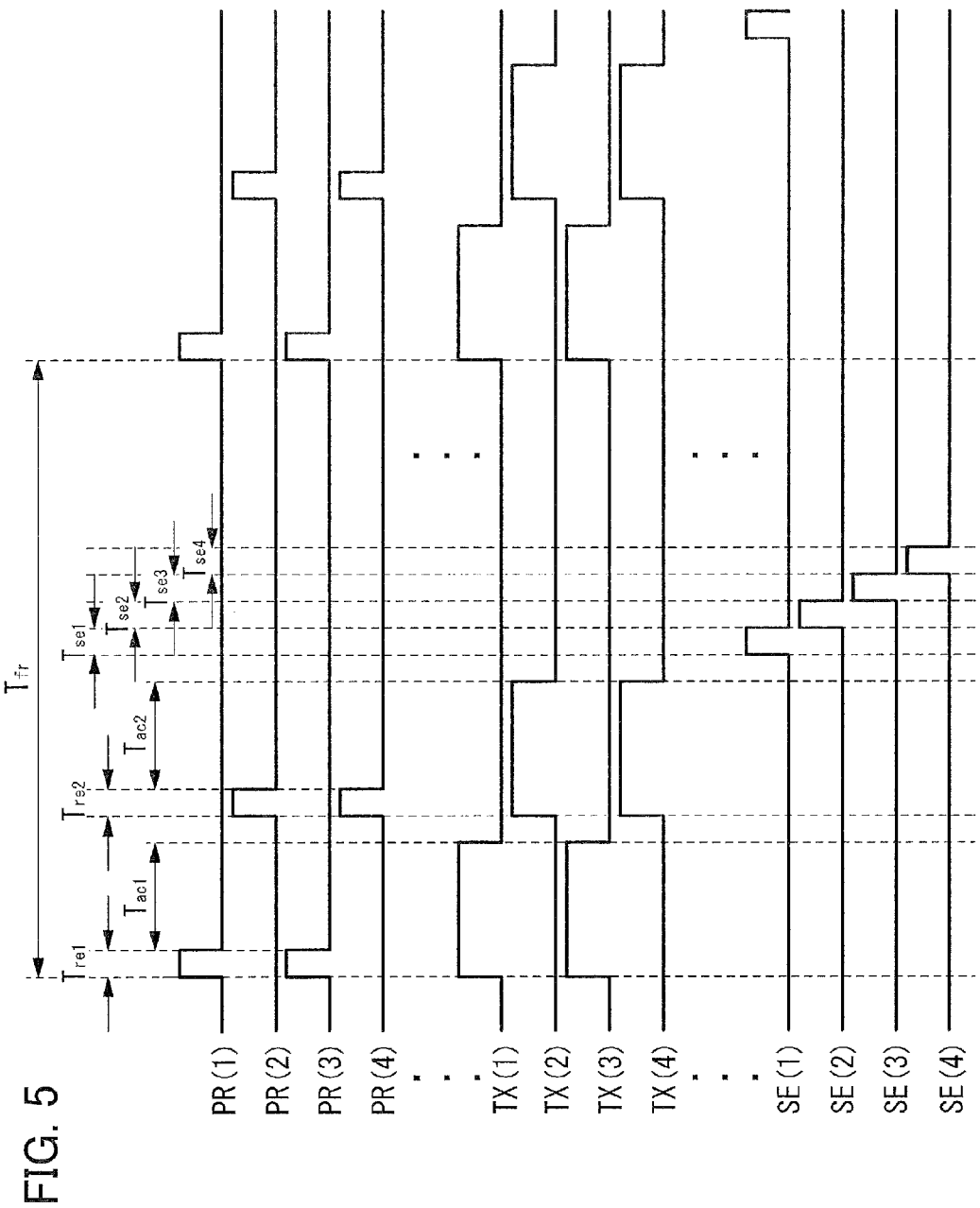
FIG. 5 is a chart showing the operation of a detection unit.

FIG. 5 is an example of a timing chart showing the operation flow of the entire detection unit 102 and shows the operation of the area surrounded by dashed-dotted lines in FIG. 4. Note that the operation of the first output circuit 111 and the second output circuit 112 is the same as that described above.

In the timing chart in FIG. 5, a signal PR(1), a signal PR(2), a signal PR(3), and a signal PR(4) correspond to the potentials of the wirings PR in the first row, the second row, the third row, and the fourth row, respectively, of pixels.

A signal TX(1), a signal TX(2), a signal TX(3), and a signal TX(4) correspond to the potentials of the wirings TX in the first row, the second row, the third row, and the fourth row, respectively, of the pixels.

A signal SE(1), a signal SE(2), a signal SE(3), and a signal SE(4) correspond to the potentials of the wirings SE in the first row, the second row, the third row, and the fourth row, respectively, of the pixels.

A period $T_{fr}$ is a period necessary for one imaging.

A period $T_{re1}$ is a period during which the first output circuits 111, which are the circuits in the first and third rows, perform the reset operation. A period $T_{ac1}$ is a period during which the first output circuits 111 perform the accumulation operation.

A period $T_{re2}$ is a period during which the second output circuits 112, which are the circuits in the second and fourth rows, perform the reset operation. A period $T_{ac2}$ is a period during which the second output circuits 112 perform the accumulation operation.

Periods $T_{se1}$ to $T_{se4}$ are periods during which the circuit in the first row (the first output circuit 111) to the circuit in the fourth row (the second output circuit 112) perform the selection operation.

In FIG. 5, the circuits in the first and third rows (the first output circuits 111) concurrently perform the reset operation or the accumulation operation, and the circuits in the second and fourth rows (the second output circuits 112) concurrently perform the reset operation or the accumulation operation. However, pixels in adjacent rows, that is, in the first and second rows, the second and third rows, and the third and fourth rows perform the reset operation or the accumulation operation in different periods. After the accumulation operation is finished, the selection operation is sequentially performed from the first row.

Here, the accumulation period of the circuits in the first and third rows (the first output circuits 111), that is, the period $T_{ac1}$ is a period during which radiation is not emitted from the radiation source 103, and the accumulation period of the circuits in the second and fourth rows (the second output circuits 112), that is, the period $T_{ac2}$ is a period during which radiation is emitted from the radiation source 103.

In other words, data (first data) corresponding to light emitted from the conversion unit 101 due to afterglow is generated in the first output circuit 111 in the period $T_{ac1}$, and data (second data) corresponding to light emitted from the conversion unit 101 due to radiation emission is generated in the second output circuit 112 in the period $T_{ac2}$. The generated data are held in the respective circuits.

Assuming that each output circuit in the detection unit 102 is sufficiently small in size, light detected by the detection circuit in the first row (the first output circuit 111) and light detected by the detection circuit in the second row (the second output circuit 112) can be considered as light emitted from the same point, that is, light generated in response to radiation emitted to the same point of the object. Similarly, light detected by the detection circuit in the third row (the first output circuit 111) and light detected by the detection circuit in the fourth row (the second output circuit 112) can be considered as light emitted from the same point, that is, light generated in response to radiation emitted to the same point of the object.

As has been described above, the amount of light due to afterglow is drastically decreased in about several milliseconds after the end of radiation emission, and then gradually decreased in general; therefore, the amount of light due to afterglow corresponding to radiation emitted before the period $T_{ac2}$ can be considered to be approximately the same in the period $T_{ac1}$ and the period $T_{ac2}$.

Consequently, with the use of a difference between the signal (first signal) obtained from the circuit in the first row (the first output circuit 111) and the signal (second signal) obtained from the circuit in the second row (the second output circuit 112), an accurate pixel signal can be generated regardless of the performance of the conversion unit 101. In addition, with the use of a difference between the signal (first signal) obtained from the circuit in the third row (the first output circuit 111) and the signal (second signal) obtained from the circuit in the fourth row (the second output circuit 112), an accurate pixel signal can be generated regardless of the performance of the conversion unit 101.

With the detection unit 102 having the above configuration, the radiation detection panel 100 can output signals for generating an accurate pixel signal regardless of the performance of the conversion unit 101.

Figure 13:
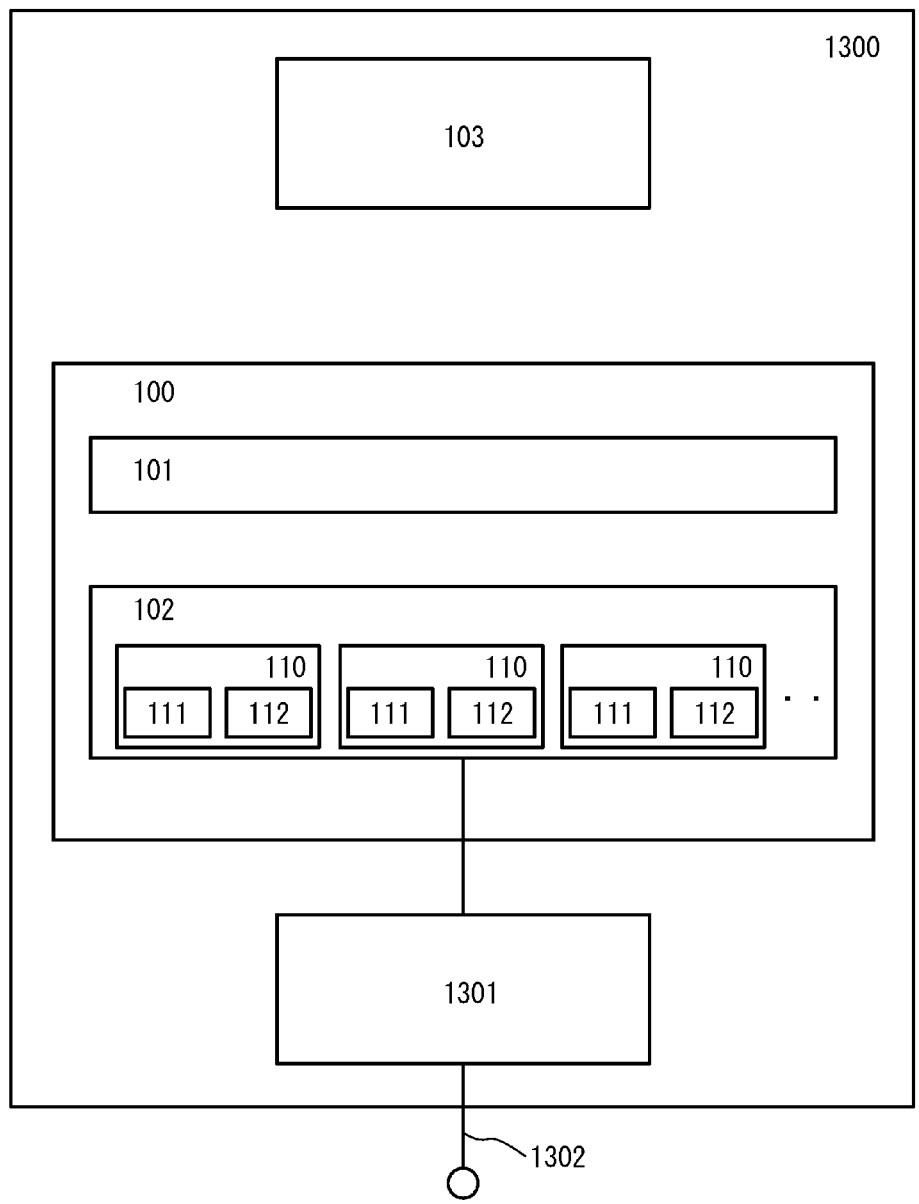
FIG. 13 illustrates the structure of a radiation imaging device.

Note that a system (hereinafter referred to as a pixel signal generation unit) that generates a pixel signal with the use of a difference between a first detection signal (the first signal) and a second detection signal (the second signal) may be provided in the radiation detection panel 100, for example, in the detection unit 102. Alternatively, as illustrated in FIG. 13, a pixel signal generation unit 1301 may be provided in a radiation imaging device 1300 together with the radiation source 103 and the radiation detection panel 100 and electrically connected to the radiation detection panel 100.

Moreover, an external output terminal 1302 electrically connected to the pixel signal generation unit 1301 is connected to a display device, and imaging data of the object is displayed. Note that the display device may be provided in the radiation imaging device 1300.

The structure of the pixel signal generation unit 1301 can be determined as appropriate by a practitioner.

Note that when the object moves largely between the period $T_{ac1}$ and the period $T_{ac2}$, not only the presence or absence of X-ray emission but also the outline of the object or the like affects the difference. For this reason, with a detection time in the period $T_{ac1}$ and the period $T_{ac2}$ of 20 ms or less, preferably 10 ms or less, further preferably 5 ms or less, noise due to movement of the object can be reduced as much as possible.

As the detection time in the period $T_{ac1}$ and the period $T_{ac2}$ becomes shorter, the amount of change in afterglow component between the period $T_{ac1}$ and the period $T_{ac2}$ becomes smaller and as a result, the amount of afterglow component in the period $T_{ac1}$ and that in the period $T_{ac2}$ can be made closer to each other. Thus, a pixel signal generated using the first signal and the second signal can constitute a more accurate image.

Note that the period $T_{ac1}$ is preferably shorter than the period $T_{ac2}$. As described above, the amount of light due to afterglow is approximately the same in the period $T_{ac1}$ and the period $T_{ac2}$; however, the amount of light due to afterglow in the period $T_{ac2}$ is sometimes smaller than that in the period $T_{ac1}$ depending on the material used for the conversion unit 101. Consequently, making the period $T_{ac1}$ shorter than the period $T_{ac2}$ can adjust a reduction in the amount of light due to afterglow in the period $T_{ac2}$.

The amount of light due to afterglow in the period $T_{ac1}$ and that in the period $T_{ac2}$ can be made closer to each other in the following manner: after the first signal is obtained in the period $T_{ac1}$ shortened as above, the second signal is obtained in the period $T_{ac2}$, and then a pixel signal is generated using a difference between the second signal and a signal obtained by integral multiple of the first signal.

Figure 15A:
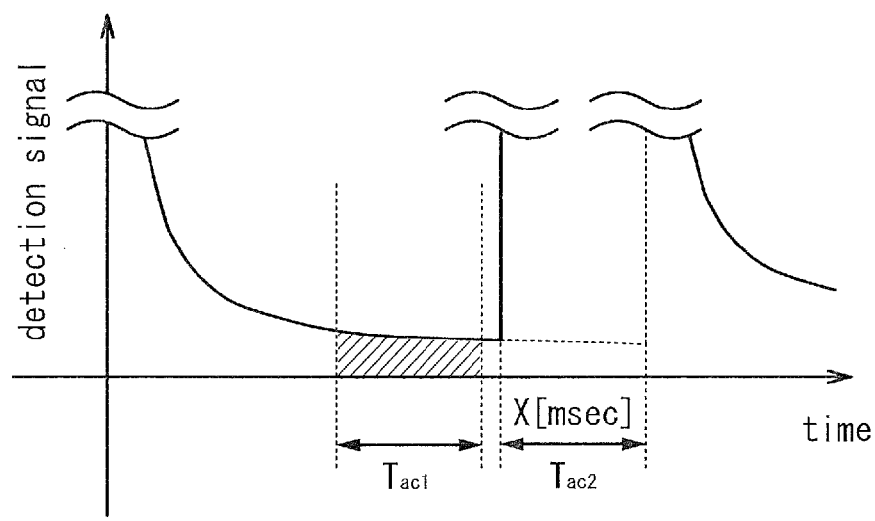
FIGS. 15A and 15B explain the concept of a method for obtaining a difference between detection signals.
Figure 15B:
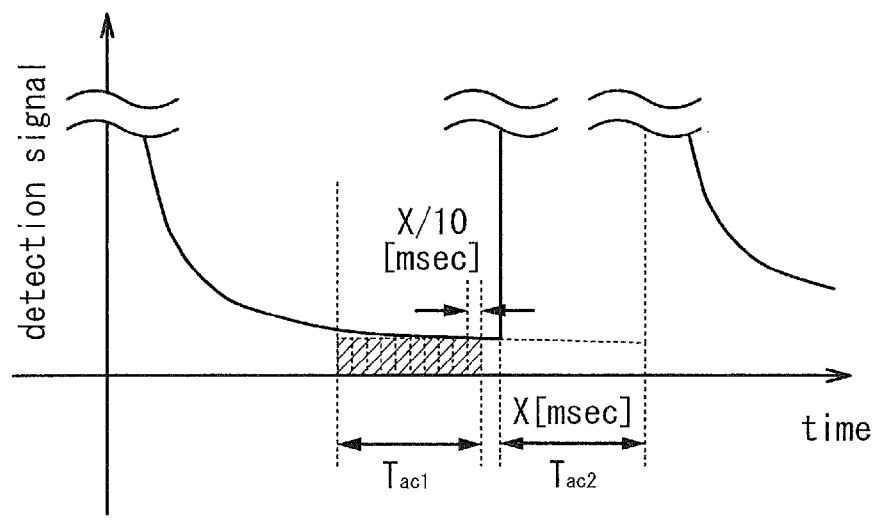

For example, assuming that the period $T_{ac2}$ is X [ms], the amount of light due to afterglow in the period $T_{ac1}$ and that in the period $T_{ac2}$ can be made closer to each other when the period $T_{ac1}$ is set $(1/10)X$ [ms], a signal obtained in the period $T_{ac1}$ is multiplied by ten (see FIG. 15B), and a difference between the resulting signal and the signal in the period $T_{ac2}$ is obtained than when the period $T_{ac1}$ is also set X [ms] to obtain a signal (see FIG. 15A) and a difference between the signals is obtained. Needless to say, the multiplier is not limited to ten.

In the case where the period $T_{ac1}$ and the period $T_{ac2}$ are adjusted as described above, the practitioner can determine, as appropriate in view of the properties of the material used for the conversion unit 101 or the like, how long the period $T_{ac1}$ is relative to the period $T_{ac2}$; how short the period $T_{ac1}$ is compared to the period $T_{ac2}$; whether the period $T_{ac1}$ is multiplied; and how many times the period $T_{ac1}$ is multiplied (what is the number to multiply the period $T_{ac1}$), for example.

This embodiment shows the example where the accumulation periods of the output circuits are the same in the first and third rows and in the second and fourth rows; however, the structure is not limited to this as long as the accumulation periods are different between adjacent rows. For example, it is possible that the accumulation periods of the output circuits are the same in the first and fourth rows and in the second and third rows so that radiation emission is stopped in the accumulation period in the first and fourth rows and radiation is emitted in the accumulation period in the second and third rows. In this case, obtaining a difference between the adjacent first and second rows and between the adjacent third and fourth rows can provide similar effects to the above.

Note that in output circuits having the same reset period and the same accumulation period (corresponding to output circuits positioned in the same row in FIG. 4), it is effective to use the shared first wiring 311 (PR) and the shared sixth wiring 316 (TX) (see FIG. 4). The use of the shared wiring can eliminate the need for a special driver circuit and simplify a peripheral circuit.

With the above-described embodiment, the radiation detection panel can output signals for generating an accurate pixel signal regardless of the performance of the conversion unit.

In the industrial field, for example, the radiation detection panel can be employed for a non-destructive imaging device using a radiation source emitting X-rays, γ-rays, β-rays, or neutron rays.

In the medical field or the like, the radiation detection panel can be used as a detection unit in a diagnostic imaging device in which a radiation source is an X-ray radiation source and a scintillator that converts X-rays into visible light is used for a conversion unit.

These imaging devices using the radiation detection panel described in this embodiment can be high-performance devices capable of obtaining high-contrast images.

Embodiment 2

Embodiment 2 shows examples of the structure of an integrator circuit used to be connected to the fourth wiring 314 (OUT).

Figure 6A:
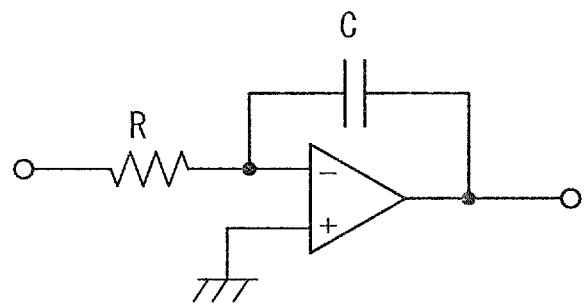
FIGS. 6A to 6C each illustrate the structure of an operational amplifier circuit.

FIG. 6A illustrates an integrator circuit including an operational amplifier circuit (also referred to as an op-amp). An inverting input terminal of the operational amplifier circuit is connected to the fourth wiring 314 (OUT) through a resistor R. A non-inverting input terminal of the operational amplifier circuit is grounded. An output terminal of the operational amplifier circuit is connected to the inverting input terminal of the operational amplifier circuit through a capacitor C.

Here, the operational amplifier circuit is assumed to be an ideal operational amplifier circuit. In other words, it is assumed that input impedance is infinite (the input terminals draw no current). Since the potential of the non-inverting input terminal and the potential of the inverting input terminal are equal in a steady state, the potential of the inverting input terminal can be considered as a ground potential.

Relational expressions $Vi=i1 \cdot R$, $i2=C \cdot dVo/dt$, and $i1+i2=0$ are satisfied, where Vi is the potential of the fourth wiring 314 (OUT), Vo is the potential of the output terminal of the operational amplifier circuit, i1 is a current flowing through the resistor R, and i2 is a current flowing through the capacitor C. Here, when charge in the capacitor C is discharged at the time t=0, the potential Vo of the output terminal of the operational amplifier circuit at the time t=t is expressed by $Vo=-(1/CR)\int Vidt$. In other words, with a longer time t (integral time), the potential (Vi) to be read can be raised and output as the detection signal Vo. Moreover, lengthening of the time t corresponds to averaging of thermal noise or the like and can increase S/N of the detection signal Vo.

In a real operational amplifier circuit, a bias current flows even when a signal is not input to the input terminals, so that an output voltage is generated at the output terminal and charge is accumulated in the capacitor C. It is therefore effective to connect a resistor in parallel with the capacitor C so that the capacitor C can be discharged.

Figure 6B:
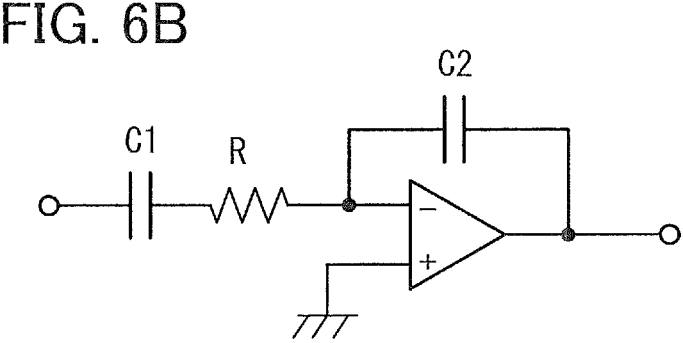

FIG. 6B illustrates an integrator circuit including an operational amplifier circuit having a structure different from that in FIG. 6A. An inverting input terminal of the operational amplifier circuit is connected to the fourth wiring 314 (OUT) through a resistor R and a capacitor C1. A non-inverting input terminal of the operational amplifier circuit is grounded. An output terminal of the operational amplifier circuit is connected to the inverting input terminal of the operational amplifier circuit through a capacitor C2.

Here, the operational amplifier circuit is assumed to be an ideal operational amplifier circuit. In other words, it is assumed that input impedance is infinite (the input terminals draw no current). Since the potential of the non-inverting input terminal and the potential of the inverting input terminal are equal in a steady state, the potential of the inverting input terminal can be considered as a ground potential.

Relational expressions $Vi=(1/C1)\int i1dt+i1 \cdot R$, $i2=C2 \cdot dVo/dt$, and $i1+i2=0$ are satisfied, where Vi is the potential of the fourth wiring 314 (OUT), Vo is the potential of the output terminal of the operational amplifier circuit, i1 is a current flowing through the resistor R and the capacitor C1, and i2 is a current flowing through the capacitor C2. Here, assuming that charge in the capacitor C2 is discharged at the time t=0, the potential Vo of the output terminal of the operational amplifier circuit at the time t=t is expressed by $Vo=-(1/C2R)\int Vidt$ when Vo<<dVo/dt, which corresponds to a high-frequency component, and $Vo=-C1/C2 \cdot Vi$ when Vo>>dVo/dt, which corresponds to a low-frequency component. In other words, by appropriately setting the capacitance ratio of the capacitor C1 to the capacitor C2, the potential (Vi) to be read can be raised and output as the detection signal Vo. Further, a high-frequency noise component of the input signal can be averaged by time integration, and S/N of the detection signal Vo can be increased.

In a real operational amplifier circuit, a bias current flows even when a signal is not input to the input terminals, so that an output voltage is generated at the output terminal and charge is accumulated in the capacitor C2. It is thus effective to connect a resistor in parallel with the capacitor C2 so that the capacitor C2 can be discharged.

Figure 6C:
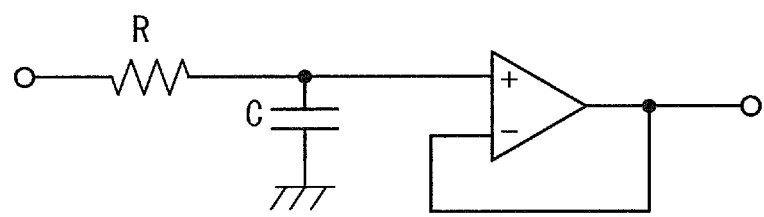

FIG. 6C illustrates an integrator circuit including an operational amplifier circuit having a structure different from those in FIGS. 6A and 6B. A non-inverting input terminal of the operational amplifier circuit is connected to the fourth wiring 314 (OUT) through a resistor R and is grounded through a capacitor C. An output terminal of the operational amplifier circuit is connected to an inverting input terminal of the operational amplifier circuit. The resistor R and the capacitor C constitute a CR integrator circuit. The operational amplifier circuit is a unity gain buffer.

The relation $Vo=(1/CR)\int Vidt$ holds, where Vi is the potential of the fourth wiring 314 (OUT) and Vo is the potential of the output terminal of the operational amplifier circuit. Although Vo is saturated at the value of Vi, a noise component included in the input signal Vi can be averaged by the CR integrator circuit, and as a result, S/N of the detection signal Vo can be increased.

The above are the examples of the structure of the integrator circuit used to be connected to the fourth wiring 314 (OUT). Connecting the integrator circuit to the fourth wiring 314 (OUT) increases S/N of the detection signal and enables weaker light to be detected; thus, the performance of the radiation detection panel can be further improved.

Embodiment 3

In Embodiment 3, the configuration and operation flow of the detection circuit 110 including the first output circuit 111 and the second output circuit 112, which are different from those in Embodiment 1, will be described with reference to FIGS. 7A and 7B, FIG. 8, FIGS. 9A and 9B, and FIG. 10.

<Different Configuration and Operation Flow (1)>

Figure 7A:
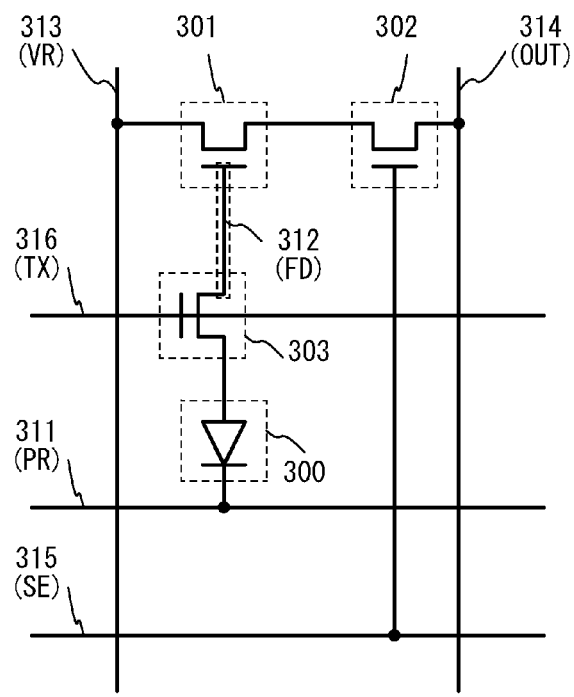
FIG. 7A illustrates the structure of a detection unit different from that in Embodiment 1.

The detection circuit 110 including the first output circuit 111 and the second output circuit 112 may have a configuration illustrated in FIG. 7A. Although the components of the detection circuit in FIG. 7A are the same as those in FIG. 3A, the configuration in FIG. 7A differs from that in FIG. 3A in that one electrode of the photoelectric conversion element 300 is electrically connected to one of the source and the drain of the third transistor 303 and the other electrode of the photoelectric conversion element 300 is electrically connected to the first wiring 311 (PR).

Note that as described in Embodiment 1, it is possible to employ any of the following structures: a capacitor or an integrator circuit is provided to connect the fourth wiring 314 (OUT); the first transistor 301 and the second transistor 302 are connected in reverse; and the third transistor 303 has a backgate.

Figure 7B:
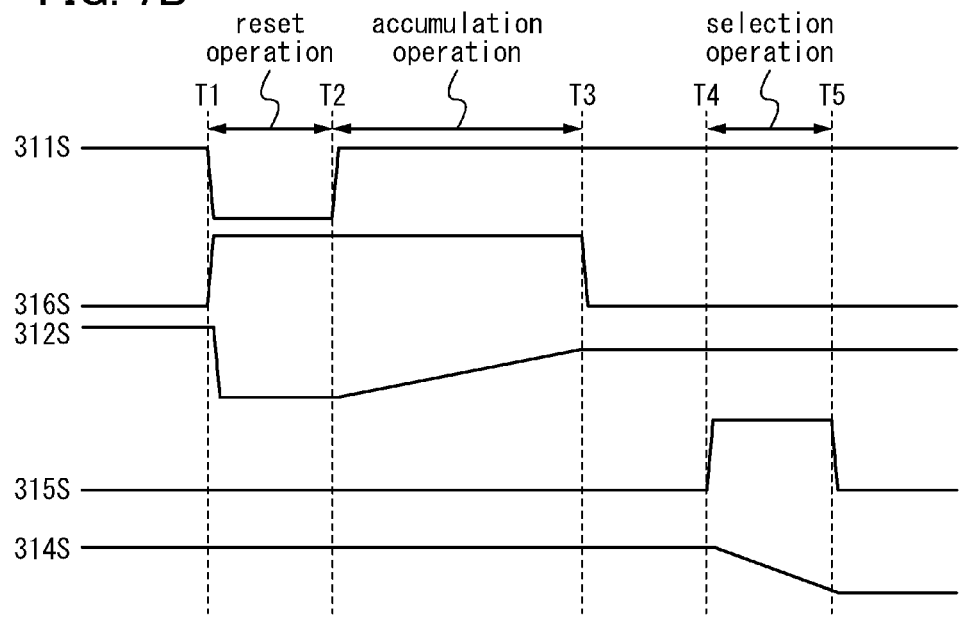
FIG. 7B is a chart showing the operation of the detection unit.

An example of operation flow of the detection circuit illustrated in FIG. 7A will be described with reference to a timing chart in FIG. 7B.

First, at the time T1, the potential of the first wiring 311 (PR) (the signal 311S) is set low and the potential of the sixth wiring 316 (TX) (the signal 316S) is set high (i.e., the reset operation starts), so that a forward bias is applied to the photoelectric conversion element 300 and the potential of the second wiring 312 (FD) (the signal 312S) becomes low. That is, the potential of the second wiring 312 (FD), which is the charge accumulation portion, is reset. Note that the potential of the fourth wiring 314 (OUT) (the signal 314S) is precharged to high level.

Next, at the time T2, the potential of the first wiring 311 (PR) (the signal 311S) is set high and the potential of the sixth wiring 316 (TX) (the signal 316S) is kept high (i.e., the reset operation finishes and the accumulation operation starts), so that a reverse bias is applied to the photoelectric conversion element 300, and as a result, the potential of the second wiring 312 (FD) (the signal 312S) starts to rise because of the reverse current. Since the reverse current increases when the photoelectric conversion element 300 is irradiated with light, the speed of increase in the potential of the second wiring 312 (FD) (the signal 312S) changes in accordance with the amount of light emitted from the conversion unit 101. In other words, the channel resistance between the source and the drain of the first transistor 301 changes in accordance with the amount of light emitted to the photoelectric conversion element 300 from the conversion unit 101.

The operations after the time T3 are similar to those in the timing chart shown in FIG. 3B. By obtaining the potential of the fourth wiring 314 (OUT) at the time T5, the amount of light emitted to the photoelectric conversion element 300 from the conversion unit 101 during the accumulation operation can be found.

<Different Configuration and Operation Flow (2)>

Figure 8:
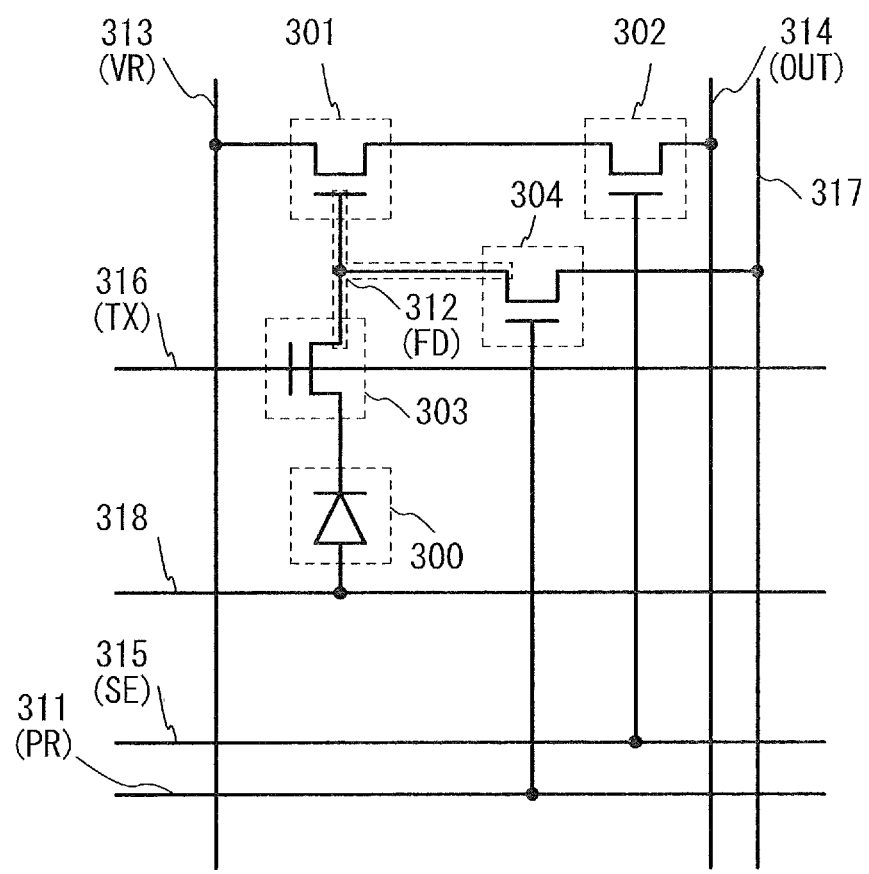
FIG. 8 illustrates the structure of a detection unit different from that in Embodiment 1.

The detection circuit 110 including the first output circuit 111 and the second output circuit 112 may have a configuration illustrated in FIG. 8. The detection circuit illustrated in FIG. 8 includes a fourth transistor 304 in addition to the components of the detection circuit illustrated in FIG. 3A. A gate of the fourth transistor 304 is electrically connected to the first wiring 311 (PR). One of a source and a drain of the fourth transistor 304 is electrically connected to the second wiring 312 (FD). The other of the source and the drain of the fourth transistor 304 is electrically connected to a seventh wiring 317. One electrode of the photoelectric conversion element 300 is electrically connected to an eighth wiring 318. Here, the eighth wiring 318 is a signal line (low potential line) for applying a reverse bias to the photoelectric conversion element 300 all the time. The seventh wiring 317 is a signal line (high potential line) for resetting the second wiring 312 (FD) to a high potential.

The fourth transistor 304 functions as a reset transistor for resetting the second wiring 312 (FD). Accordingly, unlike in the detection circuit in FIG. 3A, the reset operation using the photoelectric conversion element 300 is not performed, and a reverse bias is always applied to the photoelectric conversion element 300. The second wiring 312 (FD) can be reset by setting the potential of the first wiring 311 (PR) high, and the detection circuit in FIG. 8 can operate according to the timing chart in FIG. 3B like the detection circuit in FIG. 3A.

The fourth transistor 304 can be formed using a silicon semiconductor such as amorphous silicon, microcrystalline silicon, polycrystalline silicon, or single crystal silicon; however, when leakage current is large, the charge accumulation portion cannot hold charge long enough. For this reason, like the third transistor 303, it is preferable to use a transistor in which a semiconductor layer (at least a channel formation region) is formed using an oxide semiconductor material achieving extremely low off-state current.

Note that as described in Embodiment 1, it is possible to employ any of the following structures: a capacitor or an integrator circuit is provided to connect the fourth wiring 314 (OUT); the first transistor 301 and the second transistor 302 are connected in reverse; and the third transistor 303 has a backgate.

<Different Configuration and Operation Flow (3)>

Figure 9A:
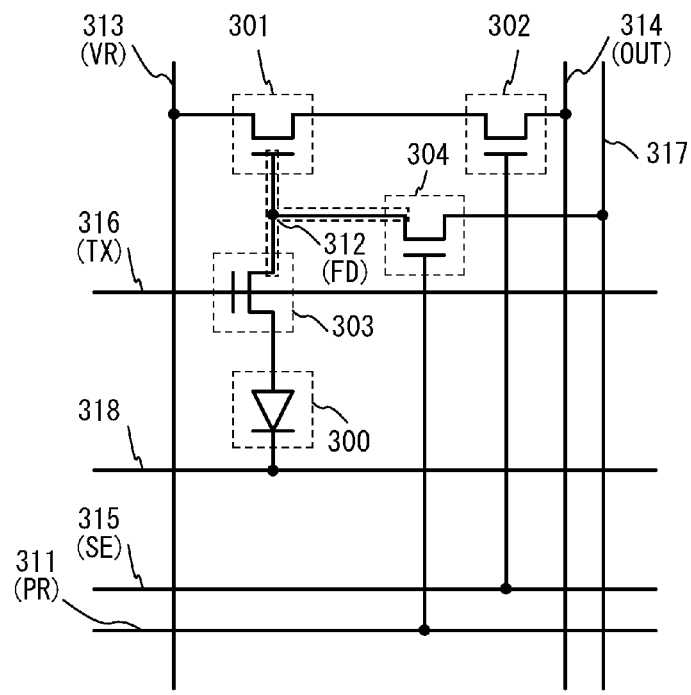
FIG. 9A illustrates the structure of a detection unit different from that in Embodiment 1.

The detection circuit 110 including the first output circuit 111 and the second output circuit 112 may have a configuration illustrated in FIG. 9A. The detection circuit illustrated in FIG. 9A includes the fourth transistor 304 in addition to the components of the detection circuit illustrated in FIG. 7A. The gate of the fourth transistor 304 is electrically connected to the first wiring 311 (PR). One of the source and the drain of the fourth transistor 304 is electrically connected to the second wiring 312 (FD). The other of the source and the drain of the fourth transistor 304 is electrically connected to a seventh wiring 317. The other electrode of the photoelectric conversion element 300 is electrically connected to the eighth wiring 318. Here, the eighth wiring 318 is a signal line (high potential line) for applying a reverse bias to the photoelectric conversion element 300 all the time. The seventh wiring 317 is a signal line (low potential line) for resetting the second wiring 312 (FD) to a low potential.

The fourth transistor 304 functions as a reset transistor for resetting the second wiring 312 (FD). Accordingly, unlike in the detection circuit in FIG. 7A, the reset operation using the photoelectric conversion element 300 is not performed, and a reverse bias is always applied to the photoelectric conversion element 300. The second wiring 312 (FD) can be reset by setting the potential of the first wiring 311 (PR) high.

Figure 9B:
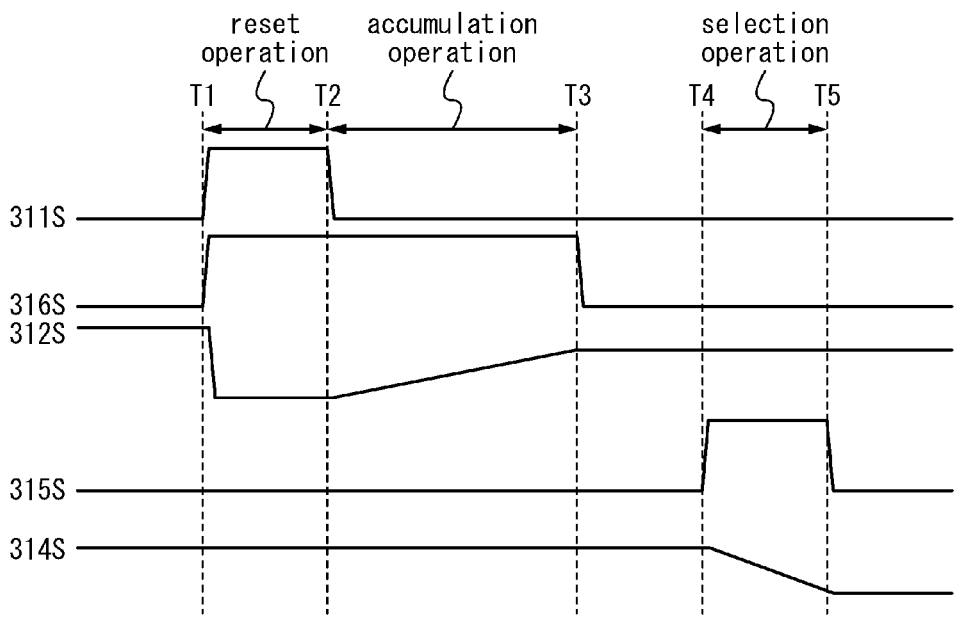
FIG. 9B is a chart showing the operation of the detection unit.

The detection circuit illustrated in FIG. 9A can operate according to a timing chart in FIG. 9B.

Although the fourth transistor 304 can be formed using a silicon semiconductor such as amorphous silicon, microcrystalline silicon, polycrystalline silicon, or single crystal silicon, the charge accumulation portion cannot hold charge long enough when leakage current is large. For this reason, like the third transistor 303, a transistor that is formed using an oxide semiconductor achieving extremely low off-state current is preferably used.

Note that as described in Embodiment 1, it is possible to employ any of the following structures: a capacitor or an integrator circuit is provided to connect the fourth wiring 314 (OUT); the first transistor 301 and the second transistor 302 are connected in reverse; and the third transistor 303 has a backgate.

<Different Configuration and Operation Flow (4)>

Figure 10:
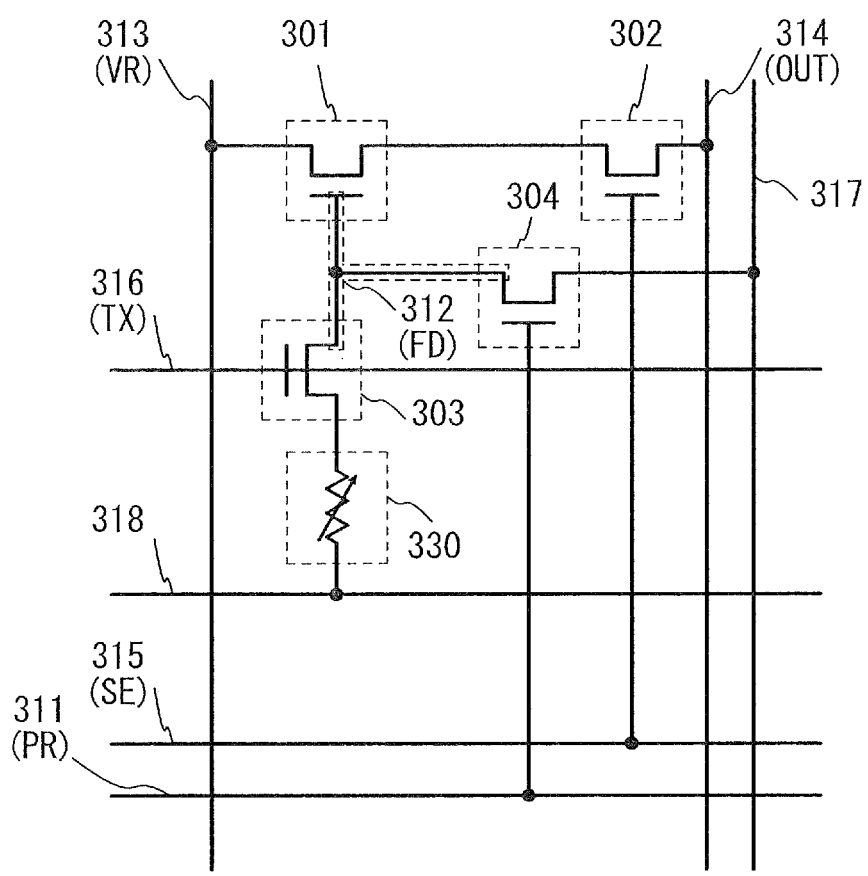
FIG. 10 illustrates the structure of a detection unit different from that in Embodiment 1.
Figure 11A:
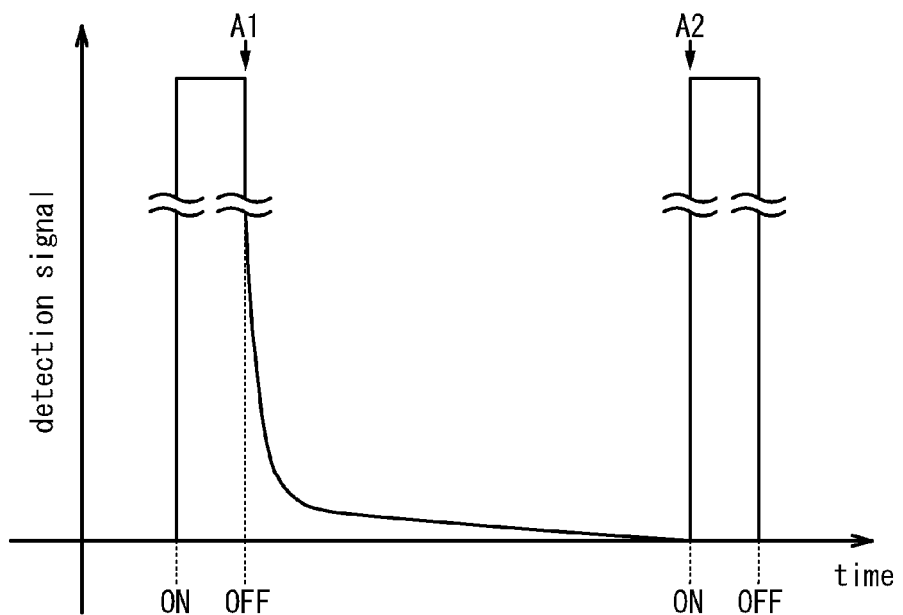
FIGS. 11A and 11B each illustrate signals output from a detection circuit.
Figure 11B:
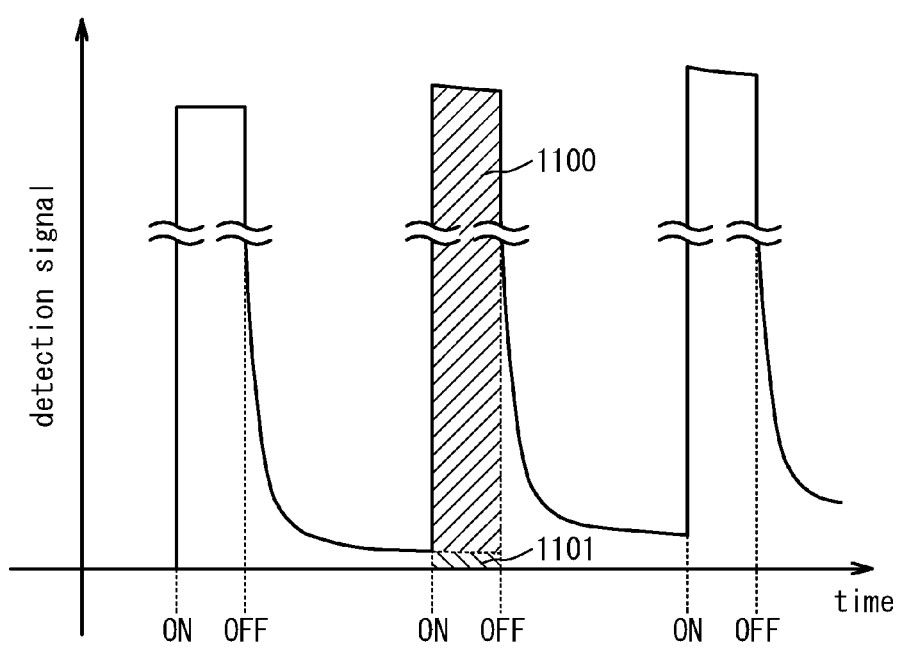
Figure 12:
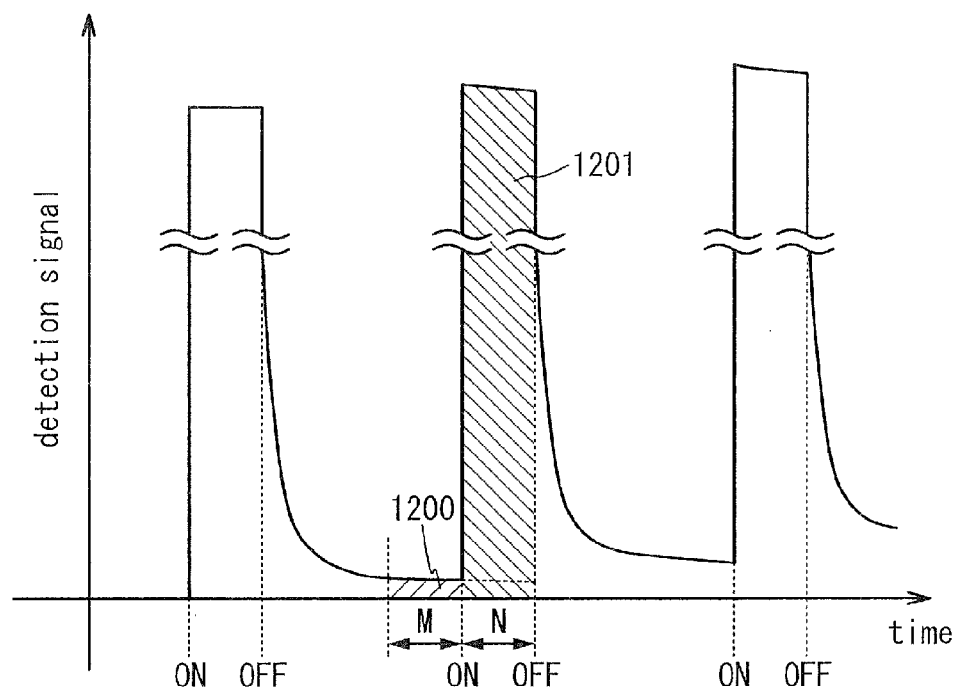
FIG. 12 explains the concept of generating a pixel signal.

The detection circuit 110 including the first output circuit 111 and the second output circuit 112 may have a configuration illustrated in FIG. 10. In the configuration for the detection circuit illustrated in FIG. 10, the photoelectric conversion element 300 in the configuration in FIG. 8 or FIG. 9A is replaced with a variable resistor 330. The variable resistor 330 can have a pair of electrodes and an i-type amorphous silicon layer provided between the pair of electrodes. Since the resistance of the i-type amorphous silicon layer varies with light emission, the potential of the second wiring 312 (FD) can be changed as in the case of using the photoelectric conversion element 300; thus, the amount of light emitted to the variable resistor 330 from the conversion unit 101 during the accumulation operation can be found.

As described in Embodiment 1, it is possible to employ any of the following structures: a capacitor or an integrator circuit is provided to connect the fourth wiring 314 (OUT); the first transistor 301 and the second transistor 302 are connected in reverse; and the third transistor 303 has a backgate.

The detection circuit illustrated in FIG. 10 can operate according to the timing chart in FIG. 3B when the eighth wiring 318 has the low potential and the seventh wiring 317 has the high potential, whereas the detection circuit can operate according to the timing chart in FIG. 9B when the eighth wiring 318 has the high potential and the seventh wiring 317 has the low potential.

The detection circuit 110 including the first output circuit 111 and the second output circuit 112 can have various configurations including the above.

Embodiment 4

In Embodiment 4, an example of the layout of the detection circuit in FIG. 3A of Embodiment 1 will be described with reference to FIGS. 14A and 14B.

FIG. 14A is a top view of the detection circuit illustrated in FIG. 3A, and FIG. 14B is a cross-sectional view along the dashed-dotted line A1-A2 in FIG. 14A.

The detection circuit includes, over a substrate 1460 on which an insulating film 1461 is formed, a conductive film 1411 serving as the first wiring 311 (PR), a conductive film 1412 serving as the second wiring 312 (FD), a conductive film 1413 serving as the third wiring 313 (VR), a conductive film 1414 serving as the fourth wiring 314 (OUT), a conductive film 1415 serving as the fifth wiring 315 (SE), and a conductive film 1416 serving as the sixth wiring 316 (TX).

The photoelectric conversion element 300 includes a p-type semiconductor film 1401, an i-type semiconductor film 1402, and an n-type semiconductor film 1403 that are stacked in this order.

The conductive film 1411, which serves as the first wiring 311 (PR), is electrically connected to the p-type semiconductor film 1401 that functions as one of the electrodes (the anode) of the photoelectric conversion element 300.

A conductive film 1418 functions as the gate of the third transistor 303 and is electrically connected to the conductive film 1416, which serves as the sixth wiring 316 (TX).

A conductive film 1419 functions as one of the source and the drain of the third transistor 303.

A conductive film 1420 functions as the other of the source and the drain of the third transistor 303.

A conductive film 1421 is electrically connected to the n-type semiconductor film 1403 and the conductive film 1419.

A conductive film 1422 functions as the gate of the first transistor 301 and is electrically connected to the conductive film 1420. Note that the conductive films 1420 and 1422 correspond to the second wiring 312 (FD) provided in the detection circuit illustrated in FIG. 3A.

A conductive film 1423 functions as the one of the source and the drain of the first transistor 301 and is electrically connected to the conductive film 1413, which serves as the third wiring 313 (VR).

A conductive film 1424 functions as the other of the source and the drain of the first transistor 301 and one of the source and the drain of the second transistor 302.

A conductive film 1425 functions as the other of the source and the drain of the second transistor 302 and is electrically connected to the conductive film 1414, which serves as the fourth wiring 314 (OUT).

A conductive film 1426 functions as the gate of the second transistor 302 and is electrically connected to the conductive film 1415, which serves as the fifth wiring 315 (SE).

The conductive films 1413, 1414, 1418, 1422, and 1426 can be formed by processing of one conductive film formed on the insulating surface into a desired shape. A gate insulating film 1428 is formed over the conductive films 1413, 1414, 1418, 1422, and 1426. Semiconductor layers 1451 to 1453 are formed over the gate insulating film 1428. The semiconductor layers 1451 to 1453 are the semiconductor layers of the first to third transistors 301 to 303. The conductive films 1411, 1415, 1416, 1419, 1420, 1423, 1424, and 1425 can be formed by processing of one conductive film formed over the semiconductor layers 1451 to 1453 and the gate insulating film 1428 into a desired shape.

An insulating film 1481 and an insulating film 1482 are formed over the conductive films 1411, 1415, 1416, 1419, 1420, 1423, 1424, and 1425. The conductive film 1421 is formed over the insulating films 1481 and 1482.

An oxide semiconductor is preferably used for the semiconductor layer 1453 of the third transistor 303. In order for the charge accumulation portion to achieve long-term storage of charge generated by irradiation of the photoelectric conversion element 300 with light, the third transistor 303 that is electrically connected to the charge accumulation portion needs to have extremely low off-state current. For this reason, the use of an oxide semiconductor material for the semiconductor layer 1453 can improve the performance of the detection circuit. Note that the charge accumulation portion refers to the second wiring 312 (FD) in the detection circuit.

In the detection circuit, the elements such as the transistors and the photoelectric conversion element 300 may overlap each other. This structure can increase the pixel density and thus can increase the resolution of an imaging device. In addition, the area of the photoelectric conversion element 300 can be increased, and the sensitivity of the imaging device can be increased as a result.

This embodiment can be combined with any of the other embodiments disclosed in this specification as appropriate.

Embodiment 5

Embodiment 5 shows a structure of the transistor using an oxide semiconductor material for a channel formation region described in Embodiment 1, a material used for the semiconductor layer of the transistor, and a fabrication method and a structure of the semiconductor layer.

<Structure of Transistor>

For example, the transistor can have the structure illustrated in the top view and the cross-sectional view of FIGS. 14A and 14B of the third transistor 303 including the semiconductor layer 1453. This structure is an example of a channel-etched bottom-gate structure, but the transistor can have a variety of other known structures such as a channel-protective bottom-gate structure, a non-self-aligned top-gate structure, and a self-aligned top-gate structure.

<Material used for Semiconductor Layer>

An oxide semiconductor material used for the semiconductor layer preferably contains at least indium (In) or zinc (Zn). In particular, the oxide semiconductor material preferably contains In and Zn. In addition, as a stabilizer for reducing variations in electric characteristics of transistors using the oxide semiconductor material, the oxide semiconductor material preferably contains gallium (Ga), tin (Sn), hafnium (Hf), and/or aluminum (Al).

As another stabilizer, the oxide semiconductor material may contain one or plural kinds of lanthanoid such as lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu).

Examples of the oxide semiconductor material to be used are indium oxide, tin oxide, zinc oxide, In—Zn-based oxide, In—Mg-based oxide, In—Ga-based oxide, In—Ga—Zn-based oxide (also referred to as IGZO), In—Al—Zn-based oxide, In—Sn—Zn-based oxide, In—Hf—Zn-based oxide, In—La—Zn-based oxide, In—Ce—Zn-based oxide, In—Pr—Zn-based oxide, In—Nd—Zn-based oxide, In—Sm—Zn-based oxide, In—Eu—Zn-based oxide, In—Gd—Zn-based oxide, In—Tb—Zn-based oxide, In—Dy—Zn-based oxide, In—Ho—Zn-based oxide, In—Er—Zn-based oxide, In—Tm—Zn-based oxide, In—Yb—Zn-based oxide, In—Lu—Zn-based oxide, In—Sn—Ga—Zn-based oxide, In—Hf—Ga—Zn-based oxide, In—Al—Ga—Zn-based oxide, In—Sn—Al—Zn-based oxide, In—Sn—Hf—Zn-based oxide, and In—Hf—Al—Zn-based oxide.

For example, an In—Ga—Zn-based oxide refers to an oxide containing In, Ga, and Zn as its main components, and there is no limitation on the composition ratio of In, Ga, and Zn. The In—Ga—Zn-based oxide may contain a metal element other than In, Ga, and Zn. The In—Ga—Zn-based oxide has sufficiently high resistance when no electric field is applied thereto, so that off-state current can be sufficiently reduced. Moreover, the In—Ga—Zn-based oxide has high mobility and thus is a semiconductor material suitable for a transistor in a radiation detection panel.

For example, an In—Ga—Zn-based oxide with an atomic ratio of In:Ga:Zn=1:1:1 (=1/3:1/3:1/3) or In:Ga:Zn=2:2:1 (=2/5:2/5:1/5), or an oxide with an atomic ratio close to the above atomic ratios can be used. Alternatively, an In—Sn—Zn-based oxide with an atomic ratio of In:Sn:Zn=1:1:1 (=1/3:1/3:1/3), In:Sn:Zn=2:1:3 (=1/3:1/6:1/2), or In:Sn:Zn=2:1:5 (=1/4:1/8:5/8) or an oxide with an atomic ratio close to the above atomic ratios may be used.

Alternatively, a material represented by $InMO_3(ZnO)_m$ (m>0, where m is not an integer) may be used as the oxide semiconductor material. Note that M represents one or more metal elements selected from Ga, Fe, Mn, and Co. Further alternatively, a material expressed by $In_2SnO_5(ZnO)_n$ (n>0, where n is an integer) may be used as the oxide semiconductor material.

<Method for Forming Semiconductor Layer>

As the semiconductor layer, a film formed using an oxide semiconductor material (hereinafter referred to as an oxide semiconductor film) can be formed in the following manner, for example: an oxide semiconductor film is formed by PVD such as sputtering or electron beam evaporation; a resist mask is formed over the film by photolithography or the like; and then, the oxide semiconductor film is selectively removed by dry etching, wet etching, or the like.

Note that if the oxide semiconductor film contains a large amount of hydrogen, the hydrogen and the oxide semiconductor are bonded to each other, so that part of the hydrogen serves as a donor and causes generation of an electron which is a carrier. As a result, the threshold voltage of the transistor shifts in the negative direction. Accordingly, the hydrogen concentration in the oxide semiconductor film is preferably lower than $5\times10^{18}$ atoms/cm$^3$, more preferably $1\times10^{18}$ atoms/cm$^3$ or lower, still more preferably $5\times10^{17}$ atoms/cm$^3$ or lower, even more preferably $1\times10^{16}$ atoms/cm$^3$ or lower. Note that the hydrogen concentration in the semiconductor layer is measured by secondary ion mass spectrometry (SIMS).

For the above reason, it is preferable that the gas used for deposition of the oxide semiconductor film do not contain impurities such as water, hydrogen, a hydroxyl group, or a hydride.

For example, a deposition gas having a purity of 6N or higher, preferably 7N or higher (i.e., an impurity concentration of 1 ppm or less, preferably 0.1 ppm or less) is used. Alternatively, a deposition gas having a dew point of −80° C. or lower, preferably −100° C. or lower is preferably used.

An entrapment vacuum pump such as a cryopump, an ion pump, or a titanium sublimation pump is preferably used to remove moisture (including water, water vapor, hydrogen, a hydroxyl group, or a hydroxide) in a deposition chamber. The evacuation unit may be a turbo molecular pump provided with a cold trap. From the deposition chamber which is evacuated with a cryopump, a hydrogen atom, a compound containing a hydrogen atom such as water ($H_2O$) (preferably, also a compound containing a carbon atom), and the like are removed, whereby the concentration of impurities such as hydrogen or moisture in the oxide semiconductor film formed in the deposition chamber can be reduced.

It is also preferable that the oxide semiconductor film contain nitrogen as little as possible. This is because nitrogen is bonded to the oxide semiconductor like hydrogen, so that part of the nitrogen serves as a donor and causes generation of an electron which is a carrier. Thus, it is preferable to use a semiconductor film having a peak of the amount of released ammonia molecules of $5.0\times10^{21}$ molecules/cm$^3$ or less, preferably $1.0\times10^{21}$ molecules/cm$^3$ or less, further preferably $8.0\times10^{20}$ molecules/cm$^3$ or less when measured by TDS after the semiconductor film is heated.

Moreover, the concentration of an alkali metal or an alkaline earth metal in the oxide semiconductor film is preferably $1\times10^{18}$ atoms/cm$^3$ or lower, more preferably $2\times10^{16}$ atoms/cm$^3$ or lower. This is because carriers might be generated when an alkali metal or an alkaline earth metal is bonded to the oxide semiconductor like hydrogen and nitrogen mentioned above, leading to an increase in off-state current of the transistor.

The oxide semiconductor film is classified roughly into a single-crystal oxide semiconductor film and a non-single-crystal oxide semiconductor film. The non-single-crystal oxide semiconductor film includes any of an amorphous oxide semiconductor film, a microcrystalline oxide semiconductor film, a polycrystalline oxide semiconductor film, a c-axis aligned crystalline oxide semiconductor (CAAC-OS) film, and the like. Note that the oxide semiconductor film may be a stacked film including two or more films of an amorphous oxide semiconductor film, a microcrystalline oxide semiconductor film, and a CAAC-OS film, for example.

The amorphous oxide semiconductor film has disordered atomic arrangement and no crystalline component. A typical example of the amorphous oxide semiconductor film is an oxide semiconductor film in which no crystal part exists even in a microscopic region, and the whole of the film is amorphous.

The microcrystalline oxide semiconductor film includes a microcrystal (also referred to as nanocrystal) with a size greater than or equal to 1 nm and less than 10 nm, for example. Thus, the microcrystalline oxide semiconductor film has a higher degree of atomic order than the amorphous oxide semiconductor film. Hence, the density of defect states of the microcrystalline oxide semiconductor film is lower than that of the amorphous oxide semiconductor film.

The oxide semiconductor film is preferably a CAAC-OS (c-axis aligned crystalline oxide semiconductor) film.

The CAAC-OS film is one of oxide semiconductor films including a plurality of crystal parts, and most of the crystal parts each fit inside a cube whose one side is less than 100 nm. Thus, there is a case where a crystal part included in the CAAC-OS film fits inside a cube whose one side is less than 10 nm, less than 5 nm, or less than 3 nm. The density of defect states of the CAAC-OS film is lower than that of the microcrystalline oxide semiconductor film. The CAAC-OS film is described in detail below.

In the following description, the term "parallel" indicates that the angle formed between two straight lines is greater than or equal to −10° and less than or equal to 10°, and accordingly also includes the case where the angle is greater than or equal to −5° and less than or equal to 5°. In addition, the term "perpendicular" indicates that the angle formed between two straight lines is greater than or equal to 80° and less than or equal to 100°, and accordingly includes the case where the angle is greater than or equal to 85° and less than or equal to 95°.

In a transmission electron microscope (TEM) image of the CAAC-OS film, a boundary between crystal parts, that is, a grain boundary is not clearly observed. Thus, in the CAAC-OS film, a reduction in electron mobility due to the grain boundary is less likely to occur.

According to the TEM image of the CAAC-OS film observed in a direction substantially parallel to a sample surface (cross-sectional TEM image), metal atoms are arranged in a layered manner in the crystal parts. Each metal atom layer has a morphology reflected by a surface over which the CAAC-OS film is formed (hereinafter, a surface over which the CAAC-OS film is formed is referred to as a formation surface) or a top surface of the CAAC-OS film, and is arranged in parallel to the formation surface or the top surface of the CAAC-OS film.

On the other hand, according to the TEM image of the CAAC-OS film observed in a direction substantially perpendicular to the sample surface (plan TEM image), metal atoms are arranged in a triangular or hexagonal configuration in the crystal parts. However, there is no regularity of arrangement of metal atoms between different crystal parts.

From the results of the cross-sectional TEM image and the plan TEM image, alignment is found in the crystal parts in the CAAC-OS film.

A CAAC-OS film is subjected to structural analysis with an X-ray diffraction (XRD) apparatus. For example, when the CAAC-OS film including an InGaZnO$_4$ crystal is analyzed by an out-of-plane method, a peak appears frequently when the diffraction angle (2θ) is around 31°. This peak is derived from the (009) plane of the InGaZnO$_4$ crystal, which indicates that crystals in the CAAC-OS film have c-axis alignment, and that the c-axes are aligned in a direction substantially perpendicular to the formation surface or the top surface of the CAAC-OS film.

On the other hand, when the CAAC-OS film is analyzed by an in-plane method in which an X-ray enters a sample in a direction substantially perpendicular to the c-axis, a peak appears frequently when 2θ is around 56°. This peak is derived from the (110) plane of the InGaZnO$_4$ crystal. Here, analysis (ϕ scan) is performed under conditions where the sample is rotated around a normal vector of a sample surface as an axis (ϕ axis) with 2θ fixed at around 56°. In the case where the sample is a single-crystal oxide semiconductor film of InGaZnO$_4$, six peaks appear. The six peaks are derived from crystal planes equivalent to the (110) plane. On the other hand, in the case of a CAAC-OS film, a peak is not clearly observed even when ϕ scan is performed with 2θ fixed at around 56°.

According to the above results, in the CAAC-OS film having c-axis alignment, while the directions of a-axes and b-axes are different between crystal parts, the c-axes are aligned in a direction parallel to a normal vector of a formation surface or a normal vector of a top surface. Thus, each metal atom layer arranged in a layered manner observed in the cross-sectional TEM image corresponds to a plane parallel to the a-b plane of the crystal.

Note that the crystal part is formed concurrently with deposition of the CAAC-OS film or is formed through crystallization treatment such as heat treatment. As described above, the c-axis of the crystal is aligned in a direction parallel to a normal vector of a formation surface or a normal vector of a top surface. Thus, for example, in the case where the shape of the CAAC-OS film is changed by etching or the like, the c-axis might not be necessarily parallel to a normal vector of a formation surface or a normal vector of a top surface of the CAAC-OS film.

The degree of crystallinity in the CAAC-OS film is not necessarily uniform. For example, in the case where crystal growth leading to the CAAC-OS film occurs from the vicinity of the top surface of the film, the degree of the crystallinity in the vicinity of the top surface is higher than that in the vicinity of the formation surface in some cases. Further, when an impurity is added to the CAAC-OS film, the crystallinity in a region to which the impurity is added is changed, and the degree of crystallinity in the CAAC-OS film varies depending on regions.

Note that when the CAAC-OS film with an InGaZnO$_4$ crystal is analyzed by an out-of-plane method, a peak of 2θ may also be observed at around 36°, in addition to the peak of 2θ at around 31°. The peak of 2θ at around 36° indicates that a crystal having no c-axis alignment is included in part of the CAAC-OS film. It is preferable that in the CAAC-OS film, a peak of 2θ appear at around 31° and a peak of 2θ do not appear at around 36°.

With the use of the CAAC-OS film in a transistor, change in electric characteristics of the transistor due to irradiation with visible light or ultraviolet light is small. Thus, the transistor has high reliability.

For example, the CAAC-OS film is formed by sputtering with a polycrystalline oxide semiconductor sputtering target. By collision of ions with the sputtering target, a crystal region included in the sputtering target may be cleaved along an a-b plane and sputtered particles having a plane parallel to the a-b plane (flat-plate-like sputtered particles or pellet-like sputtered particles) may flake off from the sputtering target. In this case, the flat-plate-like (or pellet-like) sputtered particles reach a substrate while maintaining their crystal state, whereby the CAAC-OS film can be formed.

For the deposition of the CAAC-OS film, the following conditions are preferably used.

Decay of the crystal state due to impurities can be prevented by reducing the amount of impurities entering the CAAC-OS film during the deposition, for example, by reduction in the concentration of impurities (e.g., hydrogen, water, carbon dioxide, and nitrogen) in the deposition chamber or in a deposition gas. Specifically, a deposition gas with a dew point of −80° C. or lower, preferably −100° C. or lower is used.

With higher substrate heating temperature during the deposition, migration of sputtered particles is likely to occur after the sputtered particles reach a substrate surface. Specifically, the substrate heating temperature during the deposition ranges from 100° C. to 740° C., preferably from 150° C. to 500° C. By increase in the substrate heating temperature during the deposition, when the flat-plate-like sputtered particle reaches the substrate, migration occurs on the substrate surface, so that a flat plane of the flat-plate-like sputtered particle is attached to the substrate.

It is preferable that the proportion of oxygen in the deposition gas be increased and the power be optimized in order to reduce plasma damage at the deposition. The proportion of oxygen in the deposition gas is 30 vol % or higher, preferably 100 vol %. A higher proportion of oxygen contained in the deposition gas facilitates formation of the CAAC-OS film because an unnecessary atom (e.g., a rare gas atom) does not enter the CAAC-OS film.

As an example of the sputtering target, an In—Ga—Zn—O compound target will be described below.

A polycrystalline In—Ga—Zn—O compound target is made by mixing $InO_X$ powder, $GaO_Y$ powder, and $ZnO_Z$ powder at a predetermined molar ratio, applying pressure to the mixture, and then performing heat treatment on the mixture at temperatures ranging from 1000° C. to 1500° C. Note that X, Y, and Z are each a given positive number. Here, the predetermined molar ratio of $InO_X$ powder to $GaO_Y$ powder and $ZnO_Z$ powder is, for example, 2:2:1, 8:4:3, 3:1:1, 1:1:1, 4:2:3, or 3:1:2. The kinds of powder and the molar ratio for mixing the powder can be determined as appropriate depending on the intended sputtering target.

<Structure of Semiconductor Layer>

The semiconductor layer may be a single-layer oxide semiconductor film formed using the material and the method described above, or a stack of a plurality of such oxide semiconductor films. For example, the semiconductor layer may be a stack of a first oxide semiconductor film, a second oxide semiconductor film, and a third oxide semiconductor film that have different compositions.

For example, it is possible that the first, second, and third oxide semiconductor films are formed using the same constituent elements and have different compositions. For example, the first oxide semiconductor film and the third oxide semiconductor film may have an atomic ratio of In:Ga:Zn=1:1:1, and the second oxide semiconductor film may have an atomic ratio of In:Ga:Zn=3:1:2. Alternatively, the first oxide semiconductor film and the third oxide semiconductor film may have an atomic ratio of In:Ga:Zn=1:3:2, and the second oxide semiconductor film may have an atomic ratio of In:Ga:Zn=3:1:2.

At this time, the second oxide semiconductor film preferably contains more In than Ga (In>Ga). Further, the first oxide semiconductor film and the third oxide semiconductor film preferably contain In and Ga at a proportion of In≤Ga.

In an oxide semiconductor, the s orbital of heavy metal mainly contributes to carrier transfer, and overlap of the s orbitals is likely to increase when the In content in the oxide semiconductor is increased. Therefore, an oxide having a composition of In>Ga has higher mobility than an oxide having a composition of In≤Ga. Further, the formation energy of oxygen vacancy is larger and thus oxygen vacancy is less likely to occur in Ga than in In; thus, the oxide having a composition of In≤Ga has more stable characteristics than the oxide having a composition of In>Ga.

Note that when the film that is different from the oxide semiconductor film and is in contact with the oxide semiconductor film (in FIG. 14B, the insulating film 1481 and the gate insulating film 1428, for example) is provided, impurities might be diffused into the oxide semiconductor film from the film in contact with the oxide semiconductor film. For example, if silicon, carbon, or the like contained in the insulating film 1481 or the gate insulating film 1428 is diffused into the oxide semiconductor film, electric characteristics of the transistor may be adversely affected.

However, the oxide semiconductor film has the stacked structure as described above. Specifically, an oxide semiconductor film (i.e., an oxide semiconductor film having a composition of In≤Ga, which corresponds to the first oxide semiconductor film and the third oxide semiconductor film in this embodiment) having fewer oxygen vacancies and more stable characteristics than a high-mobility oxide semiconductor film (i.e., an oxide semiconductor film having a composition of In>Ga, which corresponds to the second oxide semiconductor film in this embodiment) is formed in contact with the high-mobility oxide semiconductor film so that the high-mobility oxide semiconductor film can keep a distance from the film in contact with the oxide semiconductor film (in FIG. 14B, the insulating film 1481, the gate insulating film 1428, or the like). Consequently, adverse effect of impurity diffusion on the electric characteristics of the transistor (e.g., a reduction in mobility) can be suppressed. Thus, the mobility and reliability of the transistor can be increased.

With the use of a transistor including a semiconductor layer formed using the oxide semiconductor film described in this embodiment for at least some of the transistors in the detection circuit 110, first data and second data generated based on the amount of light incident from the conversion unit 101 can be held in the first output circuit 111 and the second output circuit 112, respectively. Thus, the radiation detection panel 100 can output signals for generating an accurate pixel signal regardless of the performance of the conversion unit 101.

This embodiment can be implemented in appropriate combination with the structures described in any of the other embodiments.

This application is based on Japanese Patent Application serial No. 2012-184985 filed with Japan Patent Office on Aug. 24, 2012, the entire contents of which are hereby incorporated by reference.

What is claimed is:
1. An imaging device comprising:
a detection unit;
a conversion unit; and
a radiation source,
wherein the conversion unit is configured to convert radiation from the radiation source into light,
wherein the detection unit comprises a plurality of detection circuits each comprising a first output circuit and a second output circuit,
wherein each of the first output circuit and the second output circuit comprises a photoelectric conversion element configured to generate charge in response to light incident from the conversion unit,
wherein the first output circuit is configured to generate first data corresponding to an amount of charge gener- ated by the photoelectric conversion element when radiation is not emitted from the radiation source, and hold the first data, wherein the second output circuit is configured to generate second data corresponding to an amount of charge generated by the photoelectric conversion element when radiation is emitted from the radiation source, and hold the second data, and wherein the detection unit is configured to output a first signal corresponding to the first data and a second signal corresponding to the second data from each of the detection circuits.

2. The imaging device according to claim 1, wherein each of the first output circuit and the second output circuit comprises a first transistor and a second transistor, wherein the first transistor of the first output circuit is configured to hold potential of a gate of the second transistor of the first output circuit corresponding to the first data, wherein the first transistor of the second output circuit is configured to hold potential of a gate of the second transistor of the second output circuit corresponding to the second data, and wherein the first transistor of each of the first output circuit and the second output circuit comprises a channel formation region comprising an oxide semiconductor material.

3. The imaging device according to claim 1, wherein the first output circuit and the second output circuit are provided adjacent to each other in each of the detection circuits.

4. The imaging device according to claim 1, wherein the first output circuit and the second output circuit are provided adjacent in an oblique direction in each of the detection circuits.

5. The imaging device according to claim 1, wherein the length of a time for the first output circuit to detect light is smaller than or equal to the length of a time for the second output circuit to detect light.

6. The imaging device according to claim 1, wherein each of the first output circuit and the second output circuit comprises a transistor comprising a channel formation region comprising an oxide semiconductor material.

7. The imaging device according to claim 1, wherein the radiation source is an X-ray radiation source, and wherein the conversion unit is a scintillator converting X-rays into visible light.

8. An imaging device comprising:

a detection unit; and a conversion unit, wherein the conversion unit is configured to convert radiation from a radiation source into light, wherein the detection unit comprises a plurality of detection circuits each comprising a first output circuit and a second output circuit, wherein each of the first output circuit and the second output circuit comprises a photoelectric conversion element configured to generate charge in response to light incident from the conversion unit, wherein the first output circuit is configured to generate first data corresponding to an amount of light incident from the conversion unit when radiation is not emitted from the radiation source, and hold the first data, wherein the second output circuit is configured to generate second data corresponding to an amount of light incident from the conversion unit when radiation is emitted from the radiation source, and hold the second data, and wherein the detection unit is configured to output a first signal corresponding to the first data and a second signal corresponding to the second data from each of the detection circuits.

9. The imaging device according to claim 8, wherein each of the first output circuit and the second output circuit comprises a first transistor and a second transistor, wherein the first transistor of the first output circuit is configured to hold potential of a gate of the second transistor of the first output circuit corresponding to the first data, wherein the first transistor of the second output circuit is configured to hold potential of a gate of the second transistor of the second output circuit corresponding to the second data, and wherein the first transistor of each of the first output circuit and the second output circuit comprises a channel formation region comprising an oxide semiconductor material.

10. The imaging device according to claim 8, wherein the first output circuit and the second output circuit are provided adjacent to each other in each of the detection circuits.

11. The imaging device according to claim 8, wherein the first output circuit and the second output circuit are provided adjacent in an oblique direction in each of the detection circuits.

12. The imaging device according to claim 8, wherein the length of a time for the first output circuit to detect light is smaller than or equal to the length of a time for the second output circuit to detect light.

13. The imaging device according to claim 8, wherein each of the first output circuit and the second output circuit comprises a transistor comprising a channel formation region comprising an oxide semiconductor material.

14. The imaging device according to claim 8, wherein the radiation source is an X-ray radiation source, and wherein the conversion unit is a scintillator converting X-rays into visible light.

15. An imaging device comprising:

a detection unit, wherein the detection unit comprises a plurality of detection circuits each comprising a first output circuit and a second output circuit, wherein each of the first output circuit and the second output circuit comprises a photoelectric conversion element configured to generate charge in response to light incident from a conversion unit configured to convert radiation from a radiation source into the light, wherein the first output circuit is configured to generate first data corresponding to an amount of light incident from the conversion unit when radiation is not emitted from the radiation source, and hold the first data, wherein the second output circuit is configured to generate second data corresponding to an amount of light incident from the conversion unit when radiation is emitted from the radiation source, and hold the second data, and wherein the detection unit is configured to output a first signal corresponding to the first data and a second signal corresponding to the second data from each of the detection circuits.

16. The imaging device according to claim 15,
wherein the first output circuit and the second output circuit are provided adjacent to each other in each of the detection circuits.

17. The imaging device according to claim 15,
wherein the first output circuit and the second output circuit are provided adjacent in an oblique direction in each of the detection circuits.

18. The imaging device according to claim 15,
wherein the length of a time for the first output circuit to detect light is smaller than or equal to the length of a time for the second output circuit to detect light.

19. The imaging device according to claim 15,
wherein each of the first output circuit and the second output circuit comprises a transistor comprising a channel formation region comprising an oxide semiconductor material.

20. The imaging device according to claim 15,
wherein the radiation source is an X-ray radiation source, and
wherein the conversion unit is a scintillator converting X-rays into visible light.

\* \* \* \* \*